(12) United States Patent
Yang et al.

(10) Patent No.: US 11,661,400 B2
(45) Date of Patent: May 30, 2023

(54) NADPH OXIDASE INHIBITORS, PHARMACEUTICAL COMPOSITION COMPRISING THE SAME, AND APPLICATION THEREOF

(71) Applicant: TAIWANJ PHARMACEUTICALS CO., LTD., Zhubei (TW)

(72) Inventors: Syaulan S. Yang, Zhubei (TW); Kuang Yuan Lee, Hsinchu (TW); Meng Hsien Liu, Toufen (TW); Yan-Feng Jiang, Kaohsiung (TW); Yu-Shiou Fan, Taipei (TW); Chiung Wen Wang, Zhubei (TW); Mei-Chi Hsu, Tainan (TW)

(73) Assignee: TAIWANJ PHARMACEUTICALS CO., LTD., Zhubei (TW)

( * ) Notice: Subject to any disclaimer, the term of this patent is extended or adjusted under 35 U.S.C. 154(b) by 0 days.

(21) Appl. No.: 17/254,565

(22) PCT Filed: Jun. 20, 2019

(86) PCT No.: PCT/US2019/038140
§ 371 (c)(1),
(2) Date: Dec. 21, 2020

(87) PCT Pub. No.: WO2019/246343
PCT Pub. Date: Dec. 26, 2019

(65) Prior Publication Data
US 2021/0276957 A1    Sep. 9, 2021

Related U.S. Application Data

(60) Provisional application No. 62/688,035, filed on Jun. 21, 2018.

(51) Int. Cl.
*C07D 215/26* (2006.01)
*C07D 223/16* (2006.01)
*C07D 401/10* (2006.01)
*C07D 409/04* (2006.01)
*C07D 491/056* (2006.01)
*C07D 495/04* (2006.01)

(52) U.S. Cl.
CPC ......... *C07D 223/16* (2013.01); *C07D 215/26* (2013.01); *C07D 401/10* (2013.01); *C07D 409/04* (2013.01); *C07D 491/056* (2013.01); *C07D 495/04* (2013.01)

(58) Field of Classification Search
CPC ............................. C07D 215/22; A61K 31/47
See application file for complete search history.

(56) References Cited

U.S. PATENT DOCUMENTS 8,877,742 B2    11/2014    Chen et al.
2013/0225612 A1    8/2013    Lambeth et al.

FOREIGN PATENT DOCUMENTS

EP    2194044    6/2010
EP    2742033    6/2014

OTHER PUBLICATIONS

STN Registy RN 1211593-37-1 (Mar. 2010).*
Hradil et al., CAPLUS Abstract 131:19164 (1999).*
Banker et al., Prodrugs, Modern Pharmaceutics, Third Edition, Revised and Expanded, pp. 451 and 596 (1996).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
STN Registry 1026416-60-7 (2008).*
STN Registry 1313738-75-8 (2011).*
STN Registry 1027039-51-5 (2008).*
STN Registry 1027067-79-3 (2008).*
STN Registry 1028289-05-5 (2008).*
"2-Phenyl-3-hydroxy-4(1H)-quinolone", PUBCHEM, Compound Summary for SID 274359412, Available Date: Dec. 18, 2015 [retrieved on Jul. 23, 2019], <URL:https://pubchem.ncbi.nlm.nih.gov/substance/274359412>.
Hussain et al., "A novel PI3K axis selective molecule exhibits potent tumor inhibition in colorectal carcinogenesis", Molecular Carcinogenesis, 2016 Wiley Periodicals, Inc., pp. 1-21.
International Search Report for PCT/US2019/038140 dated Oct. 15, 2019.
Written Opinion of the International Searching Authority for PCT/US2019/038140 dated Oct. 15, 2019.
"Partial Search Report of Europe Counterpart Application", dated Feb. 8, 2022, p. 1-p. 16.
Dmytro A. Yushchenko et al., "Synthesis and fluorescence properties of 2-aryl-3-hydroxyquinolones, a new class of dyes displaying dual fluorescence," Tetrahedron Letters, vol. 47, Nov. 2005, pp. 905-908.

(Continued)

*Primary Examiner* — Deepak R Rao
(74) *Attorney, Agent, or Firm* — JCIPRNET

(57) ABSTRACT

The present disclosure relates to a compound of Formula I, or a geometric isomer, enantiomer, diastereomer, racemate, atropisomer, pharmaceutically acceptable salt, prodrug or solvate thereof. The present disclosure further relates to a composition comprising the compound of Formula (I). The compound and the composition described herein can be used to inhibit NADPH oxidase activity.

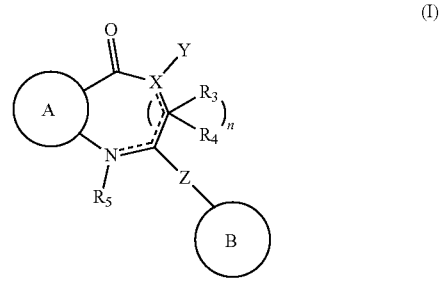

(I)

5 Claims, No Drawings

(56) References Cited

OTHER PUBLICATIONS

Kristyna Burglová et al., "Identification of Eukaryotic Translation Elongation Factor 1-α 1 Gamendazole-Binding Site for Binding of 3-Hydroxy-4(1H)-quinolinones as Novel Ligands with Anticancer Activity," J. Med. Chem., vol. 61, Mar. 2018, pp. 3027-3036.
Vasyl G. Pivovarenko et al., "A Toolbox of Chromones and Quinolones for Measuring a Wide Range of ATP Concentrations," Chemistry—A European Journal, vol. 23, Jul. 2017, pp. 11927-11934.
J. Joseph et al., "Synthesis, characterization and pharmacological studies of copper complexes of flavone derivatives as potential anti-tuberculosis agents," Journal of photochemistry & photobiology, B: Biology, vol. 162, Jun. 2016, pp. 125-145.
Petr Funk et al., "Preparation of 2-phenyl-3-hydroxyquinoline-4(1H)-one-5-carboxamides as potential anticancer and fluorescence agents," RSC Advances, vol. 5, May 2015, pp. 48861-48867.

\* cited by examiner

NADPH OXIDASE INHIBITORS, PHARMACEUTICAL COMPOSITION COMPRISING THE SAME, AND APPLICATION THEREOF

CROSS REFERENCE TO RELATED APPLICATIONS

This application is the National Phase of PCT International Application No. PCT/US2019/038140, filed on Jun. 20, 2019, which claims priority under 35 U.S.C. 119(e) to U.S. Provisional Application No. 62/688,035, filed on Jun. 21, 2018, all of which are hereby expressly incorporated by reference into the present application.

BACKGROUND

Reactive Oxygen Species (ROS) are a number of reactive molecules and free radicals derived from molecular oxygen, including superoxide anion ($.O_2^-$), peroxide ($.O_2^{-2}$), hydrogen peroxide ($H_2O_2$), hydroxyl radical ($.OH$) and hydroxyl radical ion ($OH^-$). These molecules may be produced as byproducts during the aerobic respiration or by oxidoreductase enzymes and metal catalyzed oxidation. Normally, ROS play a role in immunity and cell signaling, including apoptosis, gene expression, and the activation of cell signaling cascades. However, excessive ROS production and/or impaired ROS reduction may lead to overload of ROS and oxidative stress.

Under conditions of oxidative stress, an imbalance between the systemic manifestation of ROS and biological system's ability to neutralize the reactive intermediates or to repair the resulting damage is presented, the result of which was demonstrated to contribute to various acute and chronic diseases related to cardiovascular, inflammatory, oncological, and neurological therapeutic areas.

Several enzymes found throughout the cell are involved in ROS generation, including NADPH oxidase (NOX), xanthine oxidase, lipoxygenase, cyclooxygenases (COX) and substrate coupled nitric oxide synthetase. Among the enzymes, NOX may produce a large amount of ROS in nonphagocytic cells in both normal and pathological conditions, which is particularly worthy of attention; because by inhibiting NOX activity, one may ameliorate oxidative stress without compromising immunity of the phagocytic cells.

SUMMARY

The disclosure relates to a series of NADPH oxidase inhibitors, a pharmaceutical composition comprising the same, and a method of inhibiting NADPH oxidase (NOX) activity.

According to one embodiment, a compound according to Formula (I) is provided. The pharmaceutically acceptable salt, hydrate or solvate of this compound are also provided.

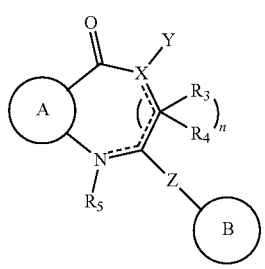

(I)

wherein A is $C_6$-$C_{20}$ aryl optionally fused with $C_1$-$C_{20}$ heterocyclyl, or $C_1$-$C_{20}$ heteroaryl optionally fused with $C_1$-$C_{20}$ heterocyclyl, and A is optionally substituted with one or more $C_1$-$C_{10}$ alkyl, $C_6$-$C_{20}$ aryl, halogen, $OR_{11}$, $C(O)R_{11}$, $C(O)OR_{11}$, $NR_{11}R_{12}$, $SO_2R_{11}$, or $SO_2(OR_{11})$; B is $C_1$-$C_{10}$ alkyl, $C_6$-$C_{20}$ aryl, $C_1$-$C_{20}$ heteroaryl or $C_1$-$C_{20}$ heterocyclyl and B is optionally substituted with one or more $C_1$-$C_{10}$ alkyl, $C_6$-$C_{20}$ aryl, $C_1$-$C_{20}$ heterocyclyl, halogen, $OR_{21}$, $C(O)R_{21}$, $C(O)OR_{21}$, $NR_{21}R_{22}$, $SO_2R_{21}$, or $SO_2(OR_{21})$, wherein said $C_1$-$C_{10}$ alkyl is optionally substituted with one or more halogen; $R_{11}$, $R_{12}$, $R_{21}$ and $R_{22}$ independently are H, O, $C_1$-$C_{10}$ alkyl, or $C_6$-$C_{20}$ aryl, wherein said $C_1$-$C_{10}$ alkyl is optionally substituted with one or more halogen; ═══ is a single bond or double bond; n is 0 or 1; X is N or C; Y is H, OH or $NH_2$; Z is nil or C(O); $R_3$ and $R_4$ independently are nil, H, $C_1$-$C_{10}$ alkyl or $C_6$-$C_{20}$ aryl; and $R_5$ is nil, H or $C_1$-$C_{10}$ alkyl.

According to other embodiment, a pharmaceutical composition is provided. The pharmaceutical composition comprises the compound according to Formula I and at least a pharmaceutically acceptable excipient or carrier.

According to still other embodiment, a method of inhibiting NADPH oxidase (NOX) is provided. The method comprises the step of administering to a cell an effective amount of the compound according to Formula I or the pharmaceutical composition comprising the compound according to Formula I and at least a pharmaceutically acceptable excipient or carrier.

DETAILED DESCRIPTION

The foregoing and other aspects of the present disclosure will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

All of the carbon, hydrogen, oxygen, Sulfur, halogen, or nitrogen involved in the groups and compounds according to the present disclosure are optionally further replaced by one or more of their corresponding isotopes, wherein the carbon isotopes include $^{12}C$, $^{13}C$ and $^{14}C$, the hydrogen isotopes include protium (H), deuterium (D, also known as heavy hydrogen) and tritium (T, also known as superheavy hydrogen), the oxygen isotopes include $^{16}O$, $^{17}O$ and $^{18}O$, the sulfur isotopes include $^{32}S$, $^{33}S$, $^{34}S$ and $^{36}S$, the nitrogen isotopes include $^{14}N$ and $^{15}N$, the fluorine isotopes include $^{17}F$ and $^{19}F$, the chlorine isotopes include $^{35}Cl$ and $^{37}Cl$, and the bromine isotopes include $^{79}Br$ and $^{81}Br$.

"Alkyl" means a linear or branched saturated aliphatic hydrocarbyl having 1 to 20 carbon atoms, preferably 1 to 10 carbon atoms. Non-limiting examples thereof include methyl, ethyl, n-propyl, isopropyl. n-butyl, sec-butyl, t-butyl, isobutyl, n-pentyl, isopentyl, neo-pentyl, n-hexyl, octyl, and various branched isomers thereof.

"Alkenyl" means a linear or branched unsaturated aliphatic hydrocarbyl having 1 to 3 carbon-carbon double bonds, and comprising 2 to 20 carbon atoms, preferably 2 to 8. Non limiting examples thereof include vinyl, propen-2-yl, buten2-yl, buten-2-yl, penten-2-yl, penten-4-yl, hexen-2-yl, hexen3-yl, hepten-2-yl, hepten-3-yl, hepten-4-yl, octen-3-yl, nonen-3-yl, decen-4-yl and hendecen-3-yl. "Alkenyl" can also include polyenes such as 1,2 propadienyl and 2,4 hexadienyl.

"Alkynyl" means a linear or branched unsaturated aliphatic hydrocarbyl having 1 to 3 carbon-carbon triple bonds, and comprising 2 to 20 carbon atoms, preferably 2 to 8 carbon atoms. Non limiting examples thereof include ethynyl, propyn-1-yl, propyn-2-yl, butyn-1-yl, butyn-2-yl, butyn-3-yl, 3.3-dimethylbutyn-2-yl, pentyn-1-yl, pentyn-2-yl, hexyn-1-yl, heptyn-1-yl, heptyn-3-yl, heptyn-4-yl, octyn-3-yl, nonyn-3-yl, decyn4-yl, hendecyn-3-yl or dodecyn-4-yl. "Alkynyl" can also include moieties comprised of multiple triple bonds such as 2,5 hexadiynyl.

"Alkoxy" means —O-alkyl. Non-limiting examples thereof include methoxy, ethoxy, n-propoxy, isopropoxy, n-butoxy, sec-butoxy, t-butoxy, n-pentyloxy, n-hexyloxy, cyclopropoxy, and cyclobutoxy. This definition applies to the alkoxys used throughout this Description.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Non-limiting examples of "haloalkyl" or "alkyl substituted with halogen" include $F_3C$—, $ClCH_2$—, $CF_3CH_2$— and $CF_3CCl_2$—.

The chemical abbreviations S(O) and S(=O) as used herein represent a sulfinyl moiety. The chemical abbreviations $SO_2$, $S(O)_2$ and $S(=O)_2$ as used herein represent a sulfonyl moiety. The chemical abbreviations C(O) and C(=O) as used herein represent a carbonyl moiety. The chemical abbreviations $CO_2$, C(O)O and C(=O)O as used herein represent an oxycarbonyl moiety. "CHO" means formyl.

"Aromatic" indicates that each of the ring atoms is essentially in the same plane and has a p-orbital perpendicular to the ring plane, and that (4n+2) π electrons, where n is a positive integer, are associated with the ring to comply with Hickel's rule. The term "aromatic ring or ring system" denotes a carbocyclic or heterocyclic ring or ring system in which the ring or at least one ring of the ring system is aromatic. The term "aromatic ring or ring system" is also referred to as "aryl". "Aryl" might include 6 to 20 carbons as ring member including phenyl, benzyl, naphthyl, and the like. Aryl can also include substituted aryl groups such as tolyl. The term "aromatic heterocyclic ring system" denotes a heterocyclic ring system in which at least one ring of the ring system is aromatic. The term "aromatic heterocyclic ring system" is also referred to as "heteroaryl". "Heteroaryl" might include 1 to 20 carbons as ring member and might further include at least one heteroatom selected from S, N, and 0.

"Carbocyclyl" means a saturated or unsaturated aromatic or non-aromatic ring, and the aromatic or non-aromatic ring may be a 3- to 8-membered monocyclic, a 4- to 12-membered bicyclic or a 10- to 20-membered tricyclic system. The carbocyclic group may have attached bridge rings or spiral rings. Non-limiting examples thereof include cyclopropyl, cyclobutyl, cyclopentyl, cyclohexyl, cycloheptyl, cyclooctyl, cyclodecyl and cyclododecyl, cyclohexenyl,

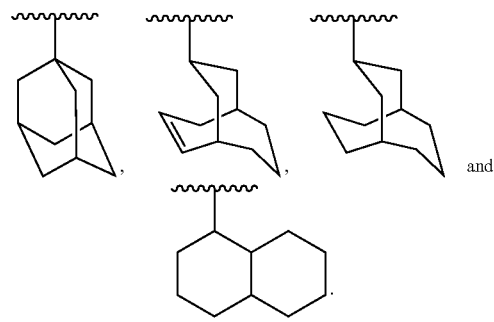

This definition applies to the carbocyclyls used throughout this Description.

"Heterocyclyl" means a substituted or unsubstituted, saturated or unsaturated, aromatic or non-aromatic ring, and the aromatic or non-aromatic ring may be a 1 to 8-membered monocyclic, a 4- to 12-membered bicyclic or a 10- to 20-membered tricyclic system, and contains at least one heteroatom selected from N, O or S. The optionally substituted N or S on the ring of a heterocyclic group may be oxidized into various oxidation States. The carbocyclic group may be attached via a heteroatom or a carbon atom, and may have attached bridge rings or spiral rings. Non-limiting examples thereof include epoxyethyl, azacyclopropyl, oxzcyclobutyl, azacyclobutyl, 1,3-dioxolane, 1,4-dioxolane, 1,3-dioxane, azacycloheptyl, pyridinyl, furyl, thiophenyl, pyranyl, N-alkylpyrrolyl, pyrimidinyl, pyrazinyl, pyridazinyl, imidazolyl, piperidinyl, hexahydropyridinyl, morpholinyl, thiomorpholinyl, 1,3-dithia-, dihydrofuryl, dihydropyranyl, dithiacyclopentyl, tetrahydrofuryl, tetrahydropyrrolyl, tetrahydroimidazolyl, tetrahydrothiazolyl, tetrahydropyranyl, benzimidazolyl, benzopyridinyl, pyrrolopyridinyl, benzodihydrofuryl, azabicyclo[3.2.1]octyl, azabicyclo[5.2.0]nonyl, azatricyclo[5.3.1.1]dodecyl, aza-adamantanyl, and oxaspiro[3.3]heptyl. This definition applies to the heterocyclyls used throughout this Description.

As used herein, the term "optional" or "optionally" means the event or situation modified by this term may but does not certainly happen, including both the case where the event or situation happens and the case not. As used herein, the term "optionally substituted" refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other. For example, "a heterocyclyl optionally substituted with alkyl" means that the alkyl may be present but is not necessarily present, including both the case where the heterocyclyl is substituted with alkyl and the case where the heterocyclyl is not substituted with alkyl.

As used herein, a "pharmaceutically acceptable" component (such as a carrier or excipient) means that the compound or composition is suitable for administration to a subject to achieve the treatments described herein, without unduly deleterious side effects in light of the severity of the disease and necessity of the treatment. "Carrier" means a material that does not cause significant stimulation to an organism and does not eliminate the biological activity and characteristics of a given compound. "Excipient" means an inert substance added into a pharmaceutical composition to facilitate administration of a compound. Non-limiting examples thereof include calcium carbonate, calcium phosphate, sugar, starch, cellulose derivatives (including microcrystalline cellulose), gelatin, vegetable oils, polyethylene glycols, diluent, a granulating agent, lubricant, binder and disintegrant.

As used herein, the term "effective amount" refers to the amount of each active agent required to confer the desired effect (e.g. inhibiting NADPH oxidase) on the subject, either alone or in combination with one or more other active agents. An effective amount varies, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A "stereoisomer" refers to an isomer of a molecule having its atoms in a different spatial arrangement, including cis-trans-isomer, enantiomer, and conformer. Compounds of this invention can exist as one or more stereoisomers. The various stereoisomers include enantiomers, diastereomers, racemates, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Embodiments of the present disclosure as described in the Summary of the Invention include those described below. In the following Embodiments, reference to "a compound of Formula I" includes the definitions of substituents specified in the Summary of the Invention unless further defined in the Embodiments.

Embodiment 1. A compound of Formula (I):

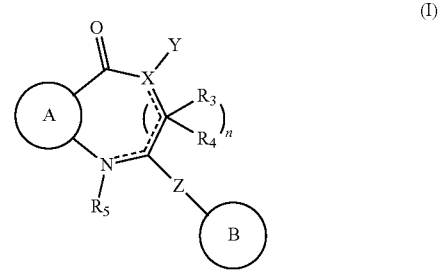

wherein A is $C_6$-$C_{20}$ aryl optionally fused with $C_1$-$C_{20}$ heterocyclyl, or $C_1$-$C_{20}$ heteroaryl optionally fused with $C_1$-$C_{20}$ heterocyclyl, and A is optionally substituted with one or more $C_1$-$C_{10}$ alkyl, $C_6$-$C_{20}$ aryl, halogen, $OR_{11}$, $C(O)R_{11}$, $C(O)OR_{11}$, $NR_{11}R_{12}$, $SO_2R_{11}$, or $SO_2(OR_{11})$; B is $C_1$-$C_{10}$ alkyl, $C_6$-$C_{20}$ aryl, $C_1$-$C_{20}$ heteroaryl or $C_1$-$C_{20}$ heterocyclyl and B is optionally substituted with one or more $C_1$-$C_{10}$ alkyl, $C_6$-$C_{20}$ aryl, $C_1$-$C_{20}$ heterocyclyl, halogen, $OR_{21}$, $C(O)R_{21}$, $C(O)OR_{21}$, $NR_{21}R_{22}$, $SO_2R_{21}$, or $SO_2(OR_{21})$, wherein said $C_1$-$C_{10}$ alkyl is optionally substituted with one or more halogen; $R_{11}$, $R_{12}$, $R_{21}$ and $R_{22}$ independently are H, O, $C_1$-$C_{10}$ alkyl, or $C_6$-$C_{20}$ aryl, wherein said $C_1$-$C_{10}$ alkyl is optionally substituted with one or more halogen; ═══ is a single bond or double bond; n is 0 or 1; X is N or C; Y is H, OH or $NH_2$; Z is nil or C(O); $R_3$ and $R_4$ independently are nil, H, $C_1$-$C_{10}$ alkyl or $C_6$-$C_{20}$ aryl; and $R_5$ is nil, H or $C_1$-$C_{10}$ alkyl.

Embodiment 2. A compound of Formula I, wherein A is $C_6$-$C_{20}$ aryl optionally fused with $C_1$-$C_{20}$ heterocyclyl, or $C_1$-$C_{20}$ heteroaryl optionally fused with $C_1$-$C_{20}$ heterocyclyl.

Embodiment 3. A compound of Formula I, wherein A is $C_6$-$C_{20}$ aryl optionally fused with $C_1$-$C_{20}$ heterocyclyl, or $C_1$-$C_{20}$ heteroaryl optionally fused with $C_1$-$C_{20}$ heterocyclyl, and A is optionally substituted with one or more $C_1$-$C_{10}$ alkyl, $C_6$-$C_{20}$ aryl, halogen, $OR_{11}$, $C(O)R_{11}$, $C(O)OR_{11}$, $NR_{11}R_{12}$, $SO_2R_{11}$, or $SO_2(OR_{11})$.

Embodiment 4. A compound of Formula I, wherein A is $C_6$-$C_{20}$ aryl.

Embodiment 5. A compound of Formula I, wherein A is $C_6$-$C_{20}$ aryl fused with $C_1$-$C_{20}$ heterocyclyl.

Embodiment 6. A compound of Formula I, wherein A is $C_1$-$C_{20}$ heteroaryl.

Embodiment 7. A compound of Formula I, wherein A is $C_1$-$C_{20}$ heteroaryl fused with $C_1$-$C_{20}$ heterocyclyl.

Embodiment 8. A compound of Formula I, wherein A is $C_6$-$C_{20}$ aryl substituted with one or more $C_1$-$C_{10}$ alkyl, $C_6$-$C_{20}$ aryl, halogen, $OR_{11}$, $C(O)R_{11}$, $C(O)OR_{11}$, $NR_{11}R_{12}$, $SO_2R_{11}$, or $SO_2(OR_{11})$.

Embodiment 9. A compound of Formula I, wherein A is $C_6$-$C_{20}$ aryl fused with $C_1$-$C_{20}$ heterocyclyl, and further substituted with one or more $C_1$-$C_{10}$ alkyl, $C_6$-$C_{20}$ aryl, halogen, $OR_{11}$, $C(O)R_{11}$, $C(O)OR_{11}$, $NR_{11}R_{12}$, $SO_2R_{11}$, or $SO_2(OR_{11})$.

Embodiment 10. A compound of Formula I, wherein A is $C_1$-$C_{20}$ heteroaryl substituted with one or more $C_1$-$C_{10}$ alkyl, $C_6$-$C_{20}$ aryl, halogen, $OR_{11}$, $C(O)R_{11}$, $C(O)OR_{11}$, $NR_{11}R_{12}$, $SO_2R_{11}$, or $SO_2(OR_{11})$.

Embodiment 11. A compound of Formula I, wherein A is $C_1$-$C_{20}$ heteroaryl fused with $C_1$-$C_{20}$ heterocyclyl, and further substituted with one or more $C_1$-$C_{10}$ alkyl, $C_6$-$C_{20}$ aryl, halogen, $OR_{11}$, $C(O)R_{11}$, $C(O)OR_{11}$, $NR_{11}R_{12}$, $SO_2R_{11}$, or $SO_2(OR_{11})$.

Embodiment 12. A compound of Formula I, wherein B is $C_1$-$C_{10}$ alkyl, $C_6$-$C_{20}$ aryl, $C_1$-$C_{20}$ heteroaryl or $C_1$-$C_{20}$ heterocyclyl.

Embodiment 13. A compound of Formula I, wherein B is $C_1$-$C_{10}$ alkyl, $C_6$-$C_{20}$ aryl or $C_1$-$C_{20}$ heteroaryl.

Embodiment 14. A compound of Formula I, wherein B is $C_1$-$C_{10}$ alkyl, $C_1$-$C_{20}$ heteroaryl or $C_1$-$C_{20}$ heterocyclyl.

Embodiment 15. A compound of Formula I, wherein B is $C_1$-$C_{10}$ alkyl, $C_6$-$C_{20}$ aryl or $C_1$-$C_{20}$ heterocyclyl.

Embodiment 16. A compound of Formula I, wherein B is $C_1$-$C_{10}$ alkyl or $C_6$-$C_{20}$ aryl.

Embodiment 17. A compound of Formula I, wherein B is $C_1$-$C_{10}$ alkyl or $C_1$-$C_{20}$ heteroaryl.

Embodiment 18. A compound of Formula I, wherein B is $C_1$-$C_{10}$ alkyl or $C_1$-$C_{20}$ heterocyclyl.

Embodiment 19. A compound of Formula I, wherein B is $C_6$-$C_{20}$ aryl or $C_1$-$C_{20}$ heteroaryl.

Embodiment 20. A compound of Formula I, wherein B is $C_6$-$C_{20}$ aryl or $C_1$-$C_{20}$ heterocyclyl.

Embodiment 21. A compound of Formula I, wherein B is $C_1$-$C_{20}$ heteroaryl or $C_1$-$C_{20}$ heterocyclyl.

Embodiment 22. A compound of Formula I, wherein B is $C_1$-$C_{10}$ alkyl.

Embodiment 23. A compound of Formula I, wherein B is $C_6$-$C_{20}$ aryl.

Embodiment 24. A compound of Formula I, wherein B is $C_1$-$C_{20}$ heteroaryl.

Embodiment 25. A compound of Formula I, wherein B is $C_1$-$C_{20}$ heterocyclyl.

Embodiment 26. A compound of any one of Embodiments 12-25, wherein B is substituted with one or more $C_1$-$C_{10}$ alkyl, $C_6$-$C_{20}$ aryl, $C_1$-$C_{20}$ heterocyclyl, halogen, $OR_{21}$, $C(O)R_{21}$, $C(O)OR_{21}$, $NR_{21}R_{22}$, $SO_2R_{21}$, or $SO_2(OR_{21})$.

Embodiment 27. A compound of Embodiment 26, wherein B is substituted with one or more $C_1$-$C_{10}$ alkyl and said $C_1$-$C_{10}$ alkyl is substituted with one or more halogen.

Embodiment 28. A compound of any one of Embodiments 8-11 and 26-27, wherein $R_{11}$, $R_{12}$, $R_{21}$ and $R_{22}$ independently are H, O, $C_1$-$C_{10}$ alkyl, or $C_6$-$C_{20}$ aryl, Embodiment 29. A compound of Embodiment 28, wherein $R_{11}$, $R_{12}$, $R_{21}$ and $R_{22}$ independently is $C_1$-$C_{10}$ alkyl and said $C_1$-$C_{10}$ alkyl is substituted with one or more halogen.

Embodiment 30. A compound of Formula I, wherein n is 0.

Embodiment 31. A compound of Formula I, wherein n is 1.

Embodiment 32. A compound of Formula I, wherein X is N or C.

Embodiment 33. A compound of Formula I, wherein X is N and Y is H, OH or $NH_2$.

Embodiment 34. A compound of Formula I, wherein X is N and Y is H.

Embodiment 35. A compound of Formula I, wherein X is C and Y is H, OH or $NH_2$.

Embodiment 36. A compound of Formula I, wherein X is C and Y is H.

Embodiment 37. A compound of Formula I, wherein X is C and Y is OH.

Embodiment 38. A compound of Formula I, wherein X is C and Y is $NH_2$.

Embodiment 39. A compound of Formula I, wherein Z is nil or C(O)

Embodiment 40. A compound of Formula I, wherein Z is nil.

Embodiment 41. A compound of Formula I, wherein Z is C(O).

Embodiment 42. A compound of Formula I, wherein $R_3$ and $R_4$ independently are nil, H, $C_1$-$C_{10}$ alkyl or $C_6$-$C_{20}$ aryl.

Embodiment 43. A compound of Formula I, wherein $R_3$ is nil and $R_4$ is nil, H, $C_1$-$C_{10}$ alkyl or $C_6$-$C_{20}$ aryl.

Embodiment 44. A compound of Formula I, wherein $R_3$ is nil and $R_4$ is nil.

Embodiment 45. A compound of Formula I, wherein $R_3$ is nil and $R_4$ is H.

Embodiment 46. A compound of Formula I, wherein $R_3$ is nil and $R_4$ is $C_1$-$C_{10}$ alkyl.

Embodiment 47. A compound of Formula I, wherein $R_3$ is nil and $R_4$ is $C_6$-$C_{20}$ aryl.

Embodiment 48. A compound of Formula I, wherein $R_3$ is H and $R_4$ is nil, H, $C_1$-$C_{10}$ alkyl or $C_6$-$C_{20}$ aryl.

Embodiment 49. A compound of Formula I, wherein $R_3$ is H and $R_4$ is nil.

Embodiment 50. A compound of Formula I, wherein $R_3$ is H and $R_4$ is H.

Embodiment 51. A compound of Formula I, wherein $R_3$ is H and $R_4$ is $C_1$-$C_{10}$ alkyl.

Embodiment 52. A compound of Formula I, wherein $R_3$ is H and $R_4$ is $C_6$-$C_{20}$ aryl.

Embodiment 53. A compound of Formula I, wherein $R_3$ is $C_1$-$C_{10}$ alkyl and $R_4$ is nil, H, $C_1$-$C_{10}$ alkyl or $C_6$-$C_{20}$ aryl.

Embodiment 54. A compound of Formula I, wherein $R_3$ is $C_1$-$C_{10}$ alkyl and $R_4$ is nil.

Embodiment 55. A compound of Formula I, wherein $R_3$ is $C_1$-$C_{10}$ alkyl and $R_4$ is H.

Embodiment 56. A compound of Formula I, wherein $R_3$ is $C_1$-$C_{10}$ alkyl and $R_4$ is $C_1$-$C_{10}$ alkyl.

Embodiment 57. A compound of Formula I, wherein $R_3$ is $C_1$-$C_{10}$ alkyl and $R_4$ is $C_6$-$C_{20}$ aryl.

Embodiment 58. A compound of Formula I, wherein $R_3$ is $C_6$-$C_{20}$ aryl and $R_4$ is nil, H, $C_1$-$C_{10}$ alkyl or $C_6$-$C_{20}$ aryl.

Embodiment 59. A compound of Formula I, wherein $R_3$ is $C_6$-$C_{20}$ aryl and $R_4$ is nil.

Embodiment 60. A compound of Formula I, wherein $R_3$ is $C_6$-$C_{20}$ aryl and $R_4$ is H.

Embodiment 61. A compound of Formula I, wherein $R_3$ is $C_6$-$C_{20}$ aryl and $R_4$ is $C_1$-$C_{10}$ alkyl.

Embodiment 62. A compound of Formula I, wherein $R_3$ is $C_6$-$C_{20}$ aryl and $R_4$ is $C_6$-$C_{20}$ aryl.

Embodiment 63. A compound of Formula I, wherein $R_5$ is nil, H or $C_1$-$C_{10}$ alkyl.

Embodiment 64. A compound of Formula I, wherein $R_5$ is nil or H.

Embodiment 65. A compound of Formula I, wherein $R_5$ is nil, or $C_1$-$C_{10}$ alkyl.

Embodiment 66. A compound of Formula I, wherein $R_5$ is H or $C_1$-$C_{10}$ alkyl.

Embodiment 67. A compound of Formula I, wherein $R_5$ is nil.

Embodiment 68. A compound of Formula I, wherein $R_5$ is H.

Embodiment 69. A compound of Formula I, wherein $R_5$ is $C_1$-$C_{10}$ alkyl.

Embodiments of this invention, including Embodiments 1-69 above as well as any other embodiments described herein, can be combined in any manner, and the descriptions of variables in the embodiments pertain not only to the compounds of Formula I but also to the starting compounds and intermediate compounds useful for preparing the compounds of Formula I. In addition, embodiments of this invention, including Embodiments 1-69 above as well as any other embodiments described herein, and any combination thereof, pertain to the compositions and methods of the present disclosure.

Combinations of Embodiments 1-69 are illustrated by:

Embodiment A. A compound of Formula (I)

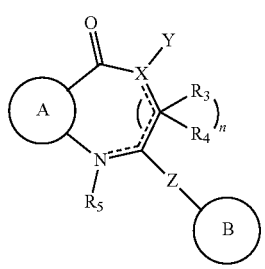

(I)

wherein

A is $C_6$-$C_{20}$ aryl optionally fused with $C_1$-$C_{20}$ heterocyclyl, or $C_1$-$C_{20}$ heteroaryl optionally fused with $C_1$-$C_{20}$ heterocyclyl, and A is optionally substituted with one or more $C_1$-$C_{10}$ alkyl, $C_6$-$C_{20}$ aryl, halogen, $OR_{11}$, $C(O)R_{11}$, $C(O)O_{Rn}$, $NR_{11}R_{12}$, $SO_2R_{11}$, or $SO_2(OR_{11})$;

B is $C_1$-$C_{10}$ alkyl, $C_6$-$C_{20}$ aryl, $C_1$-$C_{20}$ heteroaryl or $C_1$-$C_{20}$ heterocyclyl, and B is optionally substituted with one or more $C_1$-$C_{10}$ alkyl, $C_6$-$C_{20}$ aryl, $C_1$-$C_{20}$ heterocyclyl, halogen, $OR_{21}$, $C(O)R_{21}$, $C(O)OR_{21}$, $NR_{21}R_{22}$, $SO_2R_{21}$, or $SO_2(OR_{21})$, wherein said $C_1$-$C_{10}$ alkyl is optionally substituted with one or more halogen;

$R_{11}$, $R_{12}$, $R_{21}$ and $R_{22}$ independently are H, O, $C_1$-$C_{10}$ alkyl, or $C_6$-$C_{20}$ aryl, wherein said $C_1$-$C_{10}$ alkyl is optionally substituted with one or more halogen;

⸺ is a single bond or double bond;

n is 0 or 1;

X is N or C;

Y is H, OH or $NH_2$;

Z is nil or C(O);

$R_3$ and $R_4$ independently are nil, H, $C_1$-$C_{10}$ alkyl or $C_6$-$C_{20}$ aryl; and $R_5$ is nil, H or $C_1$-$C_{10}$ alkyl.

Embodiment B. A compound of Embodiment A represented by Formula (II)

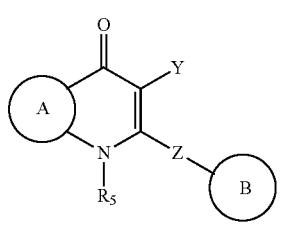

(II)

wherein

A is $C_6$-$C_{20}$ aryl optionally fused with $C_1$-$C_{20}$ heterocyclyl, or $C_1$-$C_{20}$ heteroaryl optionally fused with $C_1$-$C_{20}$ heterocyclyl, and A is optionally substituted with one or more $C_1$-$C_{10}$ alkyl, $C_6$-$C_{20}$ aryl, halogen, $OR_{11}$, $C(O)R_{11}$, $C(O)O_{Rn}$, $NR_{11}R_{12}$, $SO_2R_{11}$, or $SO_2(OR_{11})$;

B is $C_1$-$C_{10}$ alkyl, $C_6$-$C_{20}$ aryl, $C_1$-$C_{20}$ heteroaryl or $C_1$-$C_{20}$ heterocyclyl and is optionally substituted with one or more $C_1$-$C_{10}$ alkyl, $C_6$-$C_{20}$ aryl, $C_1$-$C_{20}$ heterocyclyl, halogen, $OR_{21}$, $C(O)R_{21}$, $C(O)OR_{21}$, $NR_{21}R_{22}$, $SO_2R_{21}$, or $SO_2(OR_{21})$, wherein said $C_1$-$C_{10}$ alkyl is optionally substituted with one or more halogen;

$R_{11}$, $R_{12}$, $R_{21}$ and $R_{22}$ independently are H, O, $C_1$-$C_{10}$ alkyl, or $C_6$-$C_{20}$ aryl, wherein said $C_1$-$C_{10}$ alkyl is optionally substituted with one or more halogen;

Y is OH or $NH_2$;

Z is nil or C(O); and $R_5$ is nil, H, or $C_1$-$C_{10}$ alkyl.

Embodiment C. A compound of Embodiment A represented by Formula (III)

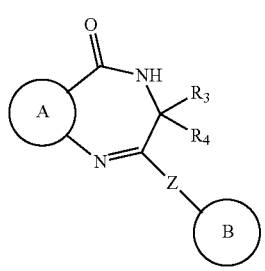

(III)

wherein

A is $C_6$-$C_{20}$ aryl optionally fused with $C_1$-$C_{20}$ heterocyclyl, or $C_1$-$C_{20}$ heteroaryl optionally fused with $C_1$-$C_{20}$ heterocyclyl, and A is optionally substituted with one or more $C_1$-$C_{10}$ alkyl, $C_6$-$C_{20}$ aryl, halogen, $OR_{11}$, $C(O)R_{11}$, $C(O)O_{Rn}$, $NR_{11}R_{12}$, $SO_2R_{11}$, or $SO_2(OR_{11})$;

B is $C_1$-$C_{10}$ alkyl, $C_6$-$C_{20}$ aryl, $C_1$-$C_{20}$ heteroaryl or $C_1$-$C_{20}$ heterocyclyl, and B is optionally substituted with one or more $C_1$-$C_{10}$ alkyl, $C_6$-$C_{20}$ aryl, $C_1$-$C_{20}$ heterocyclyl, halogen, $OR_{21}$, $C(O)R_{21}$, $C(O)OR_{21}$, $NR_{21}R_{22}$, $SO_2R_{21}$, or $SO_2(OR_{21})$, wherein said $C_1$-$C_{10}$ alkyl is optionally substituted with one or more halogen;

$R_{11}$, $R_{12}$, $R_{21}$ and $R_{22}$ independently are H, O, $C_1$-$C_{10}$ alkyl, or $C_6$-$C_{20}$ aryl, wherein said $C_1$-$C_{10}$ alkyl is optionally substituted with one or more halogen;

Z is nil or C(O); and each $R_3$ and $R_4$ independently is nil, H, $C_1$-$C_{10}$ alkyl or $C_6$-$C_{20}$ aryl.

Embodiment D. A compound of any one of Embodiments A-C wherein

A is substituted or unsubstituted $C_6$-$C_{20}$ aryl or $C_6$-$C_{20}$ aryl fused with $C_1$-$C_{20}$ heterocyclyl.

Embodiment E. A compound of any one of Embodiments A-D wherein

A is phenyl group substituted with one or more methoxy group, (dimethylamide) phenyl group, Br, $OR_{11}$, or $C(O)OR_{11}$, wherein $R_{11}$ is H, O, $C_1$-$C_{10}$ alkyl, or $C_6$-$C_{20}$ aryl, wherein said $C_1$-$C_{10}$ alkyl is optionally substituted with one or more halogen.

Embodiment F. A compound of any one of Embodiments A-C wherein
A is substituted or unsubstituted $C_1$-$C_{20}$ heteroaryl having at least one heteroatom selected from S, N, and O.
Embodiment G. A compound of Embodiment F. wherein
A is pyrroline, furan, thiophene, pyridine, pyran, or thiopyran.
Embodiment H. A compound of any one of Embodiments A-D wherein
A is substituted or unsubstituted $C_6$-$C_{20}$ aryl fused with $C_1$-$C_{20}$ heterocyclyl having at least one heteroatom selected from S, N, and O.
Embodiment I. A compound of Embodiment H wherein
A is 1,3-benzodioxole, indoline, indole, indazole, benzofuran, benzo[c]thiophene, benzo[b]thiophene, 1,2-benzisoxazole, 1,2-benzisothiazole, 2,1-benzisothiazole, benzoxazole, or benzthiazole.
Embodiment J. A compound of any one of Embodiments A-I wherein
B is substituted or unsubstituted $C_1$-$C_{10}$ alkyl.
Embodiment K. A compound of Embodiment J wherein
B is methyl, ethyl, n-propyl, i-propyl or tert-butyl group.
Embodiment L. A compound of any one of Embodiments A-I wherein
B is substituted or unsubstituted $C_6$-$C_{20}$ aryl.
Embodiment M. A compound of Embodiment L wherein
B is a phenyl group substituted with one or more methyl, $CF_3$, halogen, pyrrolidine, $OR_{21}$, $C(O)R_{21}$, $NR_{21}R_{22}$, or $SO_2R_{21}$.
Embodiment N. A compound of Embodiment M wherein
$R_{21}$ is H, O, methyl, ethyl, n-propyl, or $CF_3$; and $R_{22}$ is H or O.
Embodiment O. A compound of any one of Embodiments A-I wherein
B is substituted or unsubstituted $C_1$-$C_{20}$ heteroaryl.
Embodiment P. A compound of Embodiment O wherein
B is pyrroline, furan, thiophene, pyridine, pyran, or thiopyran.
Embodiment Q. A compound of any one of Embodiments A-P wherein
n is 0.
Embodiment R. A compound of any one of Embodiments A-Q wherein
X is C.
Embodiment S. A compound of any one of Embodiments A-R wherein
Y is H, OH or $NH_2$.
Embodiment T. A compound of any one of Embodiments A-Q wherein
X is N.
Embodiment U. A compound of Embodiment T wherein
Y is H or $NH_2$.
Embodiment V. A compound of any one of Embodiments A-U wherein
Z is nil or C(O).
Embodiment W. A compound of Embodiments A-P wherein
n is 1.
Embodiment X. A compound of Embodiment W wherein
$R_3$ and $R_4$ independently are nil, H, methyl, ethyl, n-propyl, i-propyl, tert-butyl, phenyl, benzyl, or naphthyl.
Embodiment Y. A compound of Embodiment A wherein
$R_5$ is nil, H, methyl, ethyl, n-propyl, i-propyl or tert-butyl group.

Specific embodiments include compounds of Formula I selected from a group consisting of:

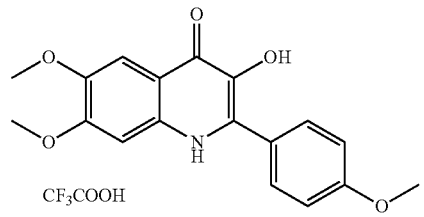

2

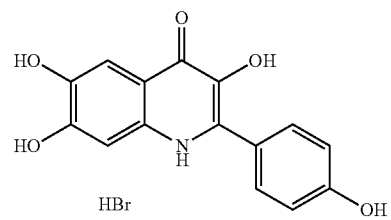

3

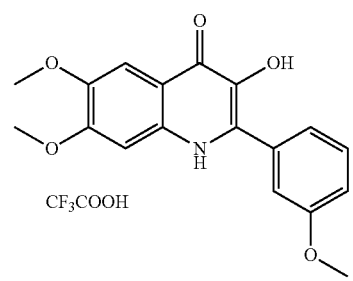

4

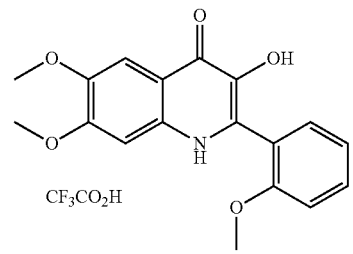

5

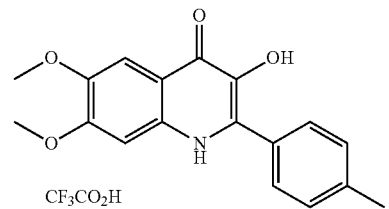

6

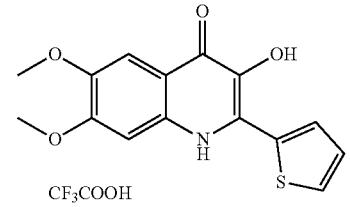

7

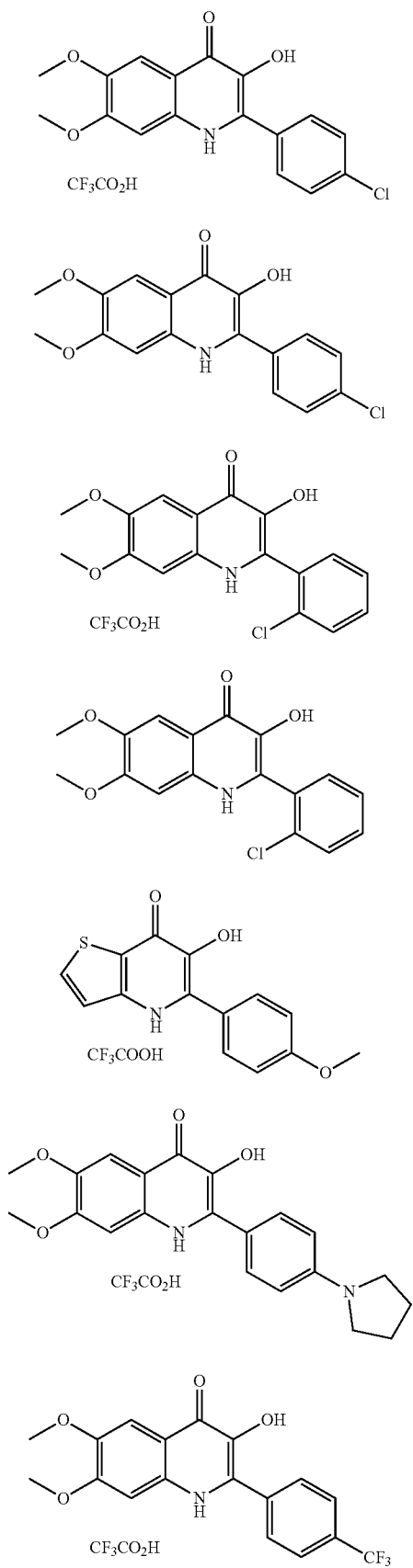

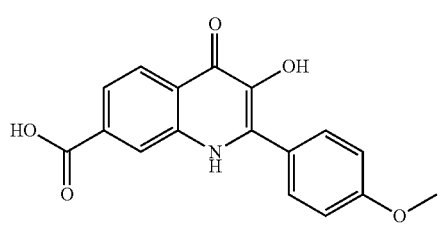
33
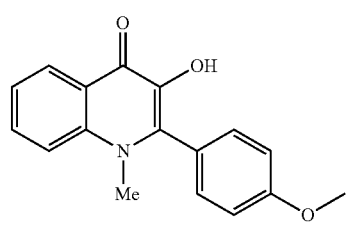
39
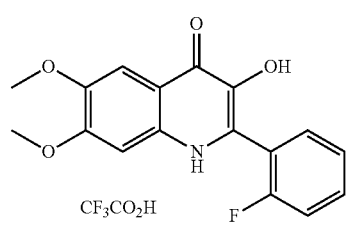
18
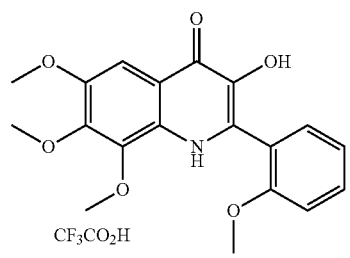
19
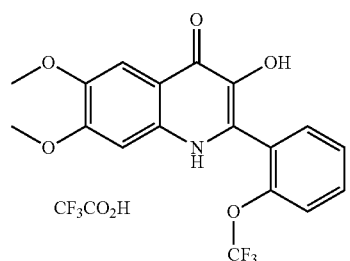
20
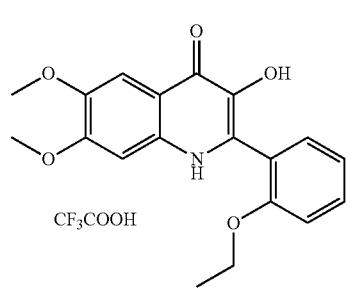
21
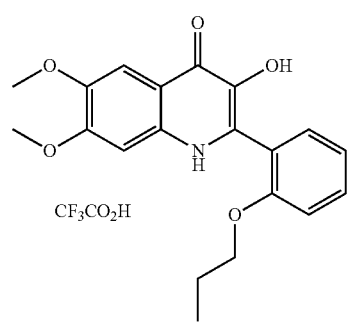
22
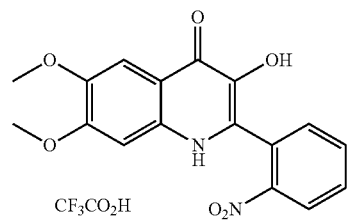
29
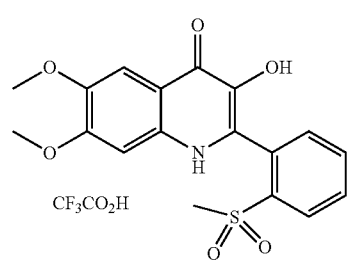
23
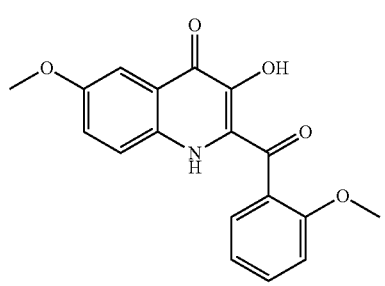
34
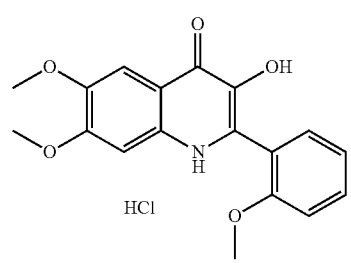
51
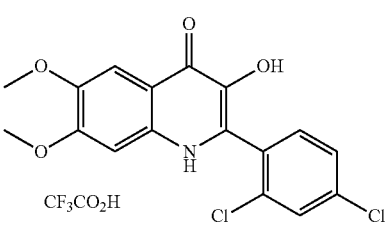
24

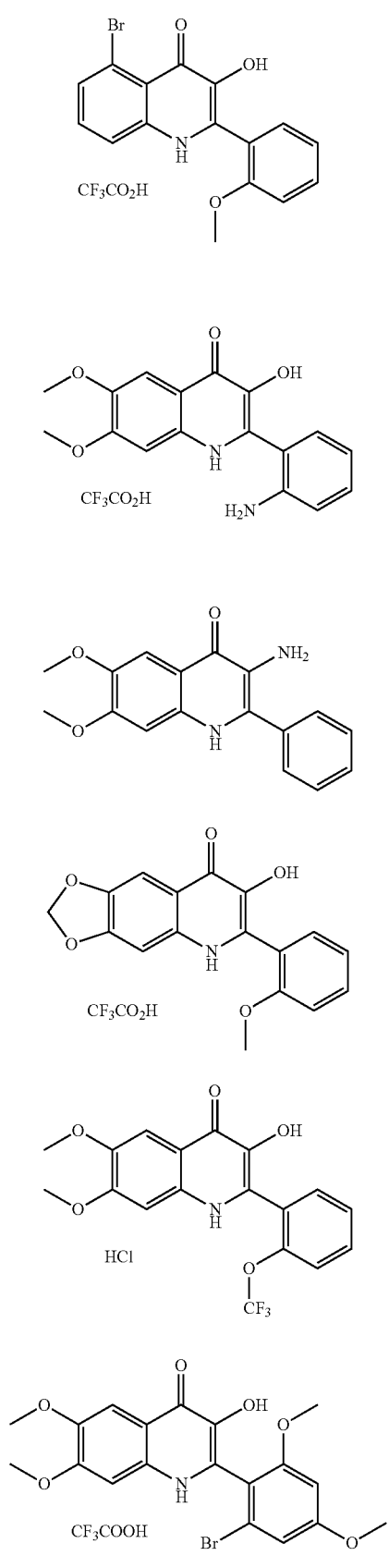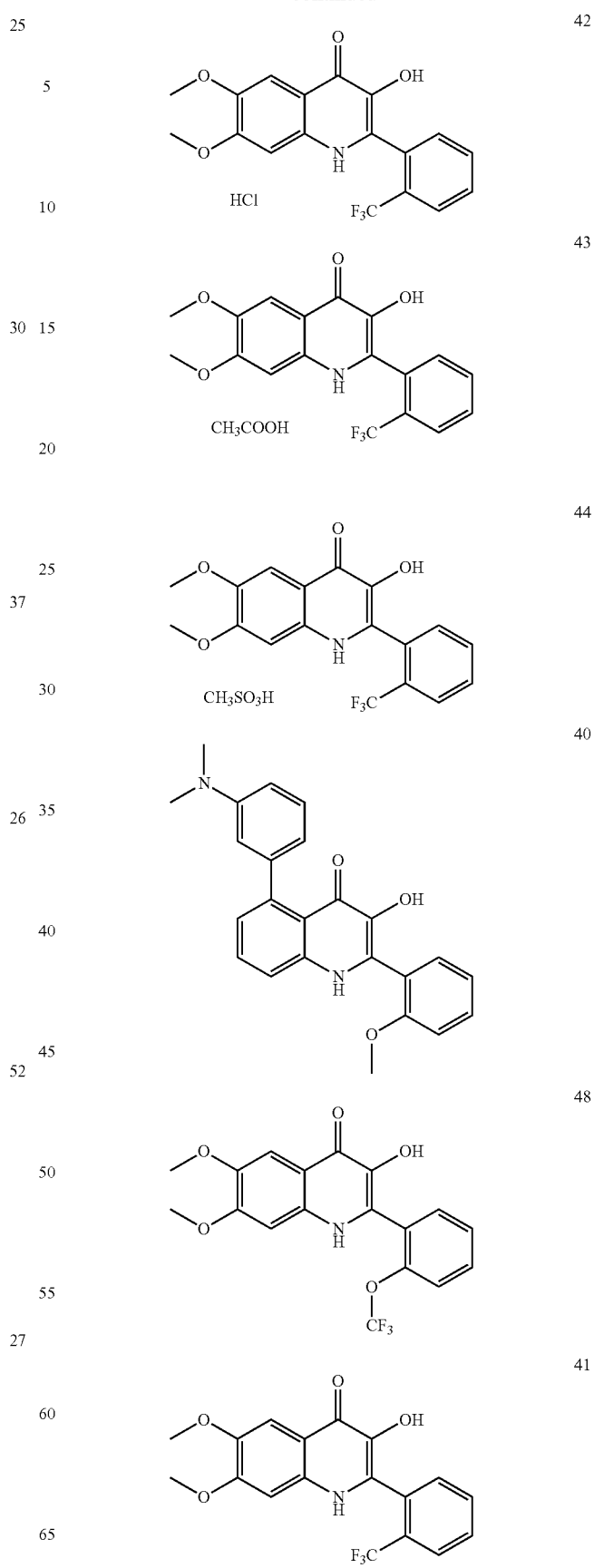

-continued

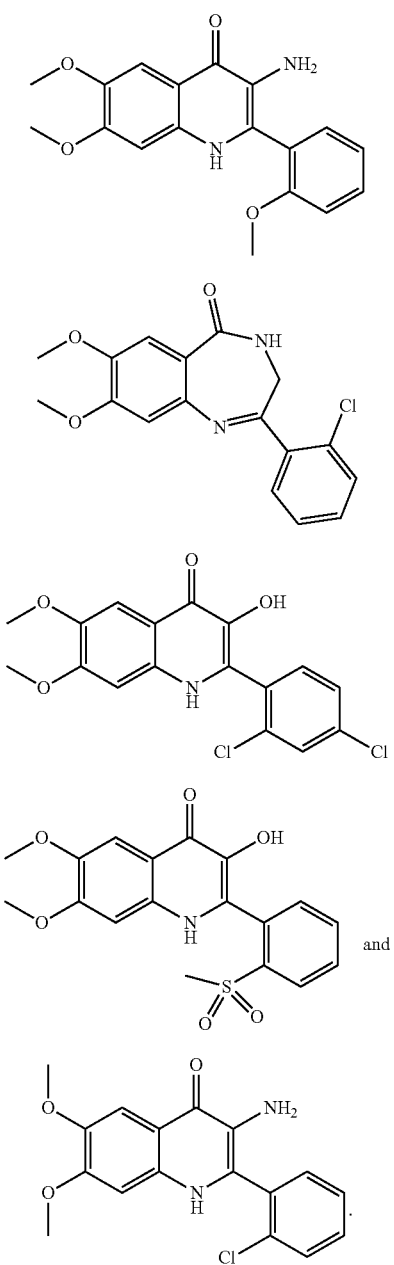

Also noteworthy as embodiments of the present disclosure are compositions comprising a compound of any of the preceding Embodiments, as well as any other embodiments described herein, and any combinations thereof. The composition can be formulated to any form of formulation that is considered to be safe, effective, and convenient for use. Preferably, the pharmaceutical composition may further comprise a pharmaceutically acceptable component as defined in the previous paragraphs. A usable pharmaceutically acceptable salt, carrier, or excipient are disclosed in various references including *Handbook of Pharmaceuticals Excipients* edited by Raymond C Rowe, Paul J Sheskey, and Marian E Quinn. In a unlimited embodiment, said pharmaceutically acceptable carrier or excipient can be selected from the group consisting of inert diluents, dispersing and/or granulating agents, surface active agents and/or emulsifiers, disintegrating agents, binding agents, preservatives, buffering agents, lubricating agents and oils. Said compositions optionally further comprising at least one additional biologically active compound or agent.

In a particular embodiment, said composition could be a pharmaceutical composition. The pharmaceutical composition might comprise but not limited to a single unit dose of the active ingredient (for instance, the compound of the present disclosure). For purposes of treatment, a dose unit can be in the form of a discrete article such as but not limited to a tablet or capsule, or can be a measurable volume of a solution, suspension or the like containing a unit dose of the active ingredient. The term "unit dose" herein refers to an amount of active ingredient intended for a single but not limited to oral, intravenous, intramuscular, cutaneous, subcutaneous, intrathecal, transdermal, implantation, sublingual, buccal, rectal, vaginal, ocular, otic, nasal, inhalation, or nebulization administration to a subject for inhibiting NADPH oxidase (NOX). The inhibitory to NOX may require periodic administration of unit doses of the compound of the present disclosure, for example one unit dose two or more times a day, one unit dose with each meal, one unit dose every four hours or other interval, or only one unit dose per day.

Further noteworthy as embodiments of the present disclosure are compositions for inhibiting NADPH oxidase (NOX) activity comprising a compound of any of the preceding Embodiments, as well as any other embodiments described herein, and any combinations thereof, and at least one of a pharmaceutically acceptable excipient or carrier selected from the group consisting of inert diluents, dispersing and/or granulating agents, surface active agents and/or emulsifiers, disintegrating agents, binding agents, preservatives, buffering agents, lubricating agents, and/or oils, said compositions optionally further comprising at least one additional biologically active compound or agent. Embodiments of the invention further include methods for inhibiting NADPH oxidase (NOX) activity in cell comprising administering to the cell an effective amount of the compound or the pharmaceutical composition of any of the preceding Embodiments (e.g., as a composition described herein).

EXAMPLES

One or more of the following methods and variations as described in Schemes I-XII can be used to prepare the compounds of Formula I. The definitions of substituents in the compounds below are as defined above unless otherwise noted. The following abbreviations are used: DCM is dichloromethane, DMF is N,N-dimethylformamide, DMSO is dimethyl sulfoxide, EA is ethyl acetate, MeOH is methanol, TFA is trifluoroacetic acid, and THF is tetrahydrofuran. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

A. Synthesis of Compounds

Variations on the following general synthetic methods will be readily apparent to those of ordinary skill in the art and are deemed to be within the scope of the present disclosure.

A-1. Synthesis of Compounds 2-20 and 24-27

As explained in details below, Compounds 2-20 and 24-27 are synthesized by the method depicted in Scheme I below.

Scheme I

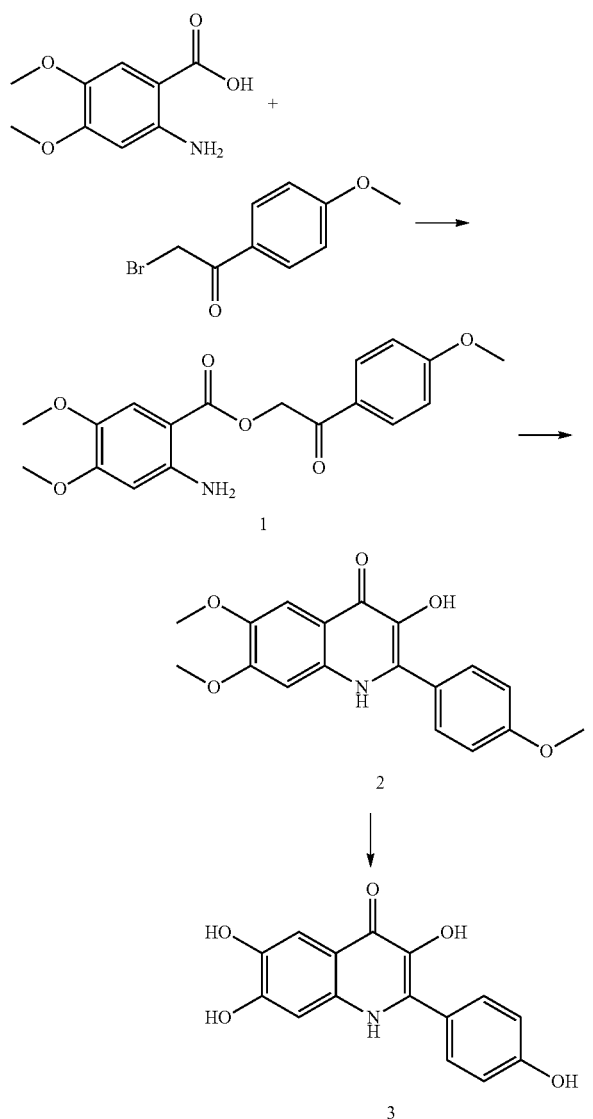

Step 1: Preparation of 2-(4-methoxyphenyl)-2-oxoethyl 2-amino-4,5-dimethoxybenzoate

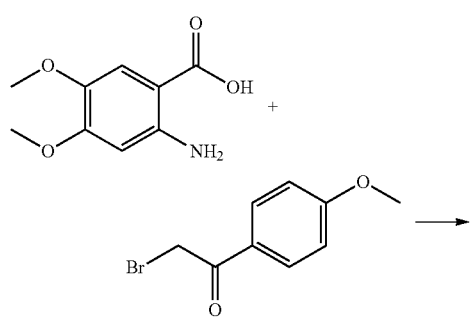

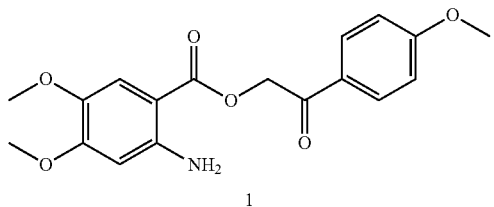

2-amino-4,5-dimethoxylbenzoic acid (1.97 g, 10 mmol) was dissolved in DMF (20 mL), and to the solution was added potassium carbonate (1.38, 10 mmol). The reaction mixture was heated at 90° C. and stirred for 1 hr. Then the solution was cooled to 20° C. and p-methoxy-2-bromoacetophenone (2.4 g, 10.5 mmol) was added. The slightly exothermic reaction took place and the temperature increased to 25° C. to 32° C. in 5 minutes. After stirring for 30 minutes the reaction mixture was heated to 50° C. and kept at this temperature for 30 minutes. The content of the flask was then poured into a 100 g mixture of water and ice. The precipitated solid material was collected by filtration, washed with water and dried. The dried solid was further recrystallized with ethanol to give Compound 1 (2-(4-methoxyphenyl)-2-oxoethyl 2-amino-4,5-dimethoxybenzoate) with a yield of 3.3 g (95%).

Step 2: Preparation of 3-hydroxy-6,7-dimethoxy-2-(4-methoxyphenyl) quinolin-4(1H)-one 2,2,2-trifluoroacetate

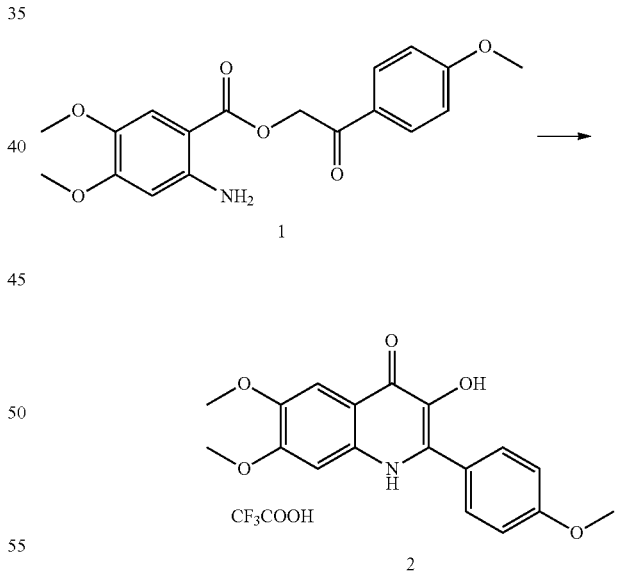

A solution of Compound 1 (0.6 g, 1.74 mmol) in TFA was heated to reflux for overnight, until reaction completed. Furthermore, the reaction mixture was cooled to room temperature, and TFA was removed in vacuo. The residue was added ice-water and stirred for 30 minutes. The solid was collected and washed by $H_2O$ and methanol to obtain Compound 2 (3-hydroxy-6,7-dimethoxy-2-(4-methoxyphenyl) quinolin-4(1H)-one 2,2,2-trifluoroacetate) with a yield of 0.5 g (87%).

Step 3: Preparation of 3,6,7-trihydroxy-2-(4-hydroxyphenyl) quinolin-4(1H)-one hydrobromide

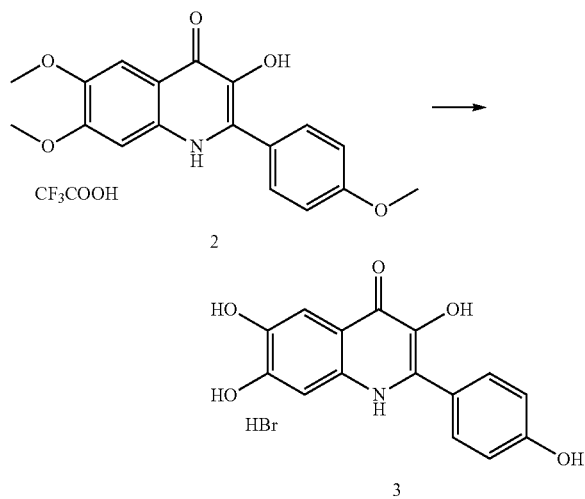

A suspension of Compound 2 (0.2 g, 0.6 mmol) in 20 mL HBr (47%) was heated to 100° C. under an atmosphere of dry nitrogen for 23 hr. The solvents were evaporated under reduced pressure and the product was crystallized (by MeOH/EA=1:3). Compound 3 (3,6,7-trihydroxy-2-(4-hydroxyphenyl) quinolin-4(1H)-one hydrobromide) is obtained with a yield of 25%.

Similarly, by replacing the p-methoxy-2-bromoacetophenone in Step 1, Compounds 4-20 and 24-27 can be prepared by the steps described above.

A-2. Synthesis of Compounds 21 and 22

Step 1A: Preparation of 2-bromo-1-(2-ethoxyphenyl) ethan-1-one

Scheme II

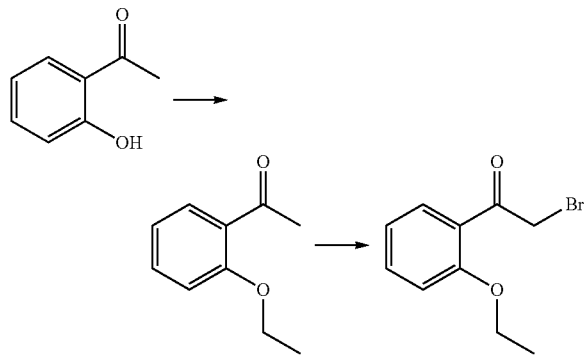

To a suspension of 1-(2-hydroxyphenyl)ethan-1-one (2.0 g, 14.69 mmol), anhydrous $K_2CO_3$ (2.6 g, 18.8 mmol) and in DMF (80 ml) was added bromoethane (5 mL, 67 mmol). The mixture was heated at 50° C. until the starting ketone was completely consumed. After cooling to room temperature, the mixture was filtered, and the solvent was removed by rotary evaporation. The residue was purified by flash chromatography. The product is 1-(2-ethoxyphenyl) ethan-1-one with n-hexane/EA (9:1) as eluent, in the presence of colorless oil. The yield is 95%.

In addition, 1-(2-ethoxyphenyl) ethan-1-one (2.55 g, 15.53 mmol) was dissolved in $Et_2O$ (40 mL) and bromine (0.7 mL, 14 mmol) was added dropwise while stirring stir the mixture in the dark at ambient temperature. Wash the reaction mixture with a saturated aqueous $Na_2CO_3$ solution. The product is dried over $MgSO_4$, filtered, collected the filtrate, and removed the volatiles under reduced pressure to provide the compound 2-bromo-1-(2-ethoxyphenyl) ethan-1-one, which was purified by flash chromatography (n-hexane/EA=9:1) with a yield of 1.8 g (48%).

The obtained compound were then used in Steps 1-3 of A-1 in replace of the p-methoxy-2-bromoacetophenone to prepare Compounds 21 and 22.

A-3. Synthesis of Compound 23

Step 1A: Preparation of 2-bromo-1-(2-(methylsulfonyl)phenyl) ethan-1-one

Scheme III

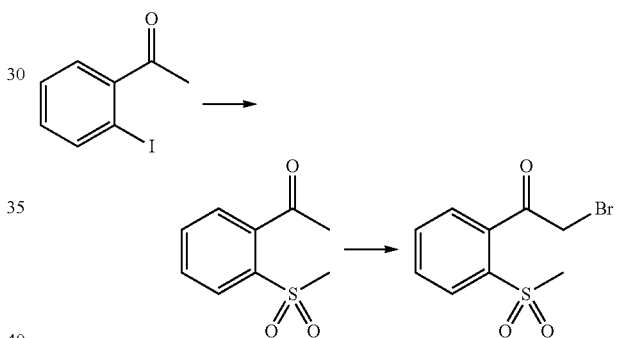

A mixture of 1-(2-iodophenyl) ethan-1-one (1.0 g, 4.06 mmol), sodium methanesulfunate (0.83 g, 8.12 mmol) and copper iodide (77 mg, 0.4 mmol) in 10 mL of DMSO was heated to 100° C. under argon. The cooled mixture was partitioned by EA and water. The organic layer was separated, and the aqueous layer was extracted with EA twice. The combined organic layers were washed with brine, dried over $MgSO_4$, and concentrated in vacuo to afford the product, 1-(2-(methylsulfonyl)phenyl) ethan-1-one, which is yellow solid with a yield of 0.77 g (95%).

To the stirred mixture copper (II) bromide (0.22 g, 0.98 mmol) in EA (6 ml) was added solution of 1-(2-(methylsulfonyl)phenyl)ethan-1-one (0.1 g, 0.5 mmol) in EA (10 ml) dropwise under the room temperature. After addition was finished, the mixture was heated at 80° C. for 18 hours. After that, the mixture was cooled to room temperature, filtered and precipitate was washed by EA (10 ml). The EA solution was treated with water, the organic phase was separated and dried over $Na_2SO_4$, and concentrated in vacuo. The crude product, 2-bromo-1-(2-(methylsulfonyl) phenyl) ethan-1-one, which was purified by column chromatography (DCM/Hexanes=2/1) to give the purified product with a yield of 0.115 g (82%).

The obtained compound were then used in Steps 1-3 of A-1 in replace of the p-methoxy-2-bromoacetophenone to prepare Compound 23.

A-4. Synthesis of Compounds 29 and 30

Preparation of 2-(2-aminophenyl)-3-hydroxy-6,7-dimethoxyquinolin-4(1H)-one

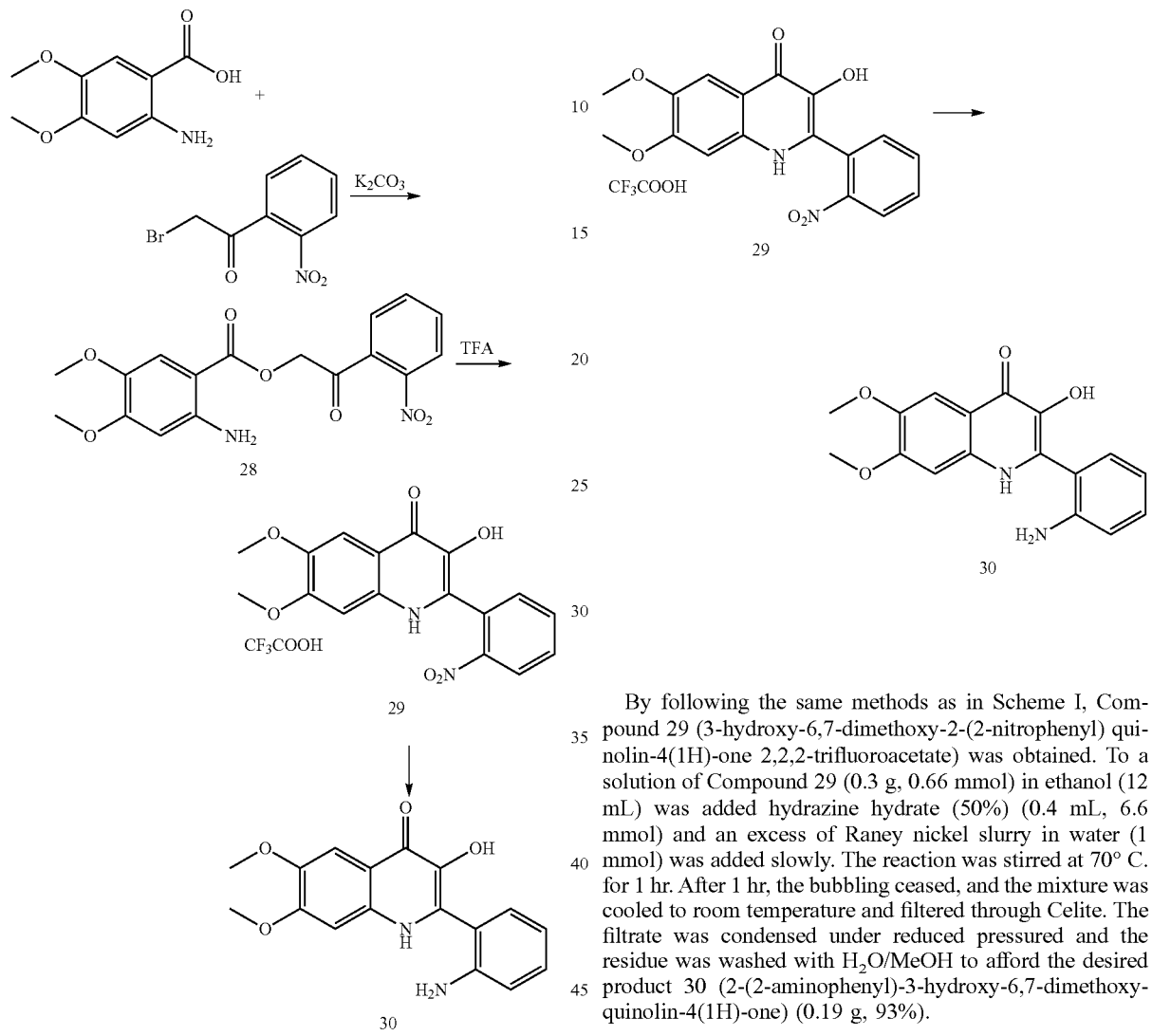

By following the same methods as in Scheme I, Compound 29 (3-hydroxy-6,7-dimethoxy-2-(2-nitrophenyl) quinolin-4(1H)-one 2,2,2-trifluoroacetate) was obtained. To a solution of Compound 29 (0.3 g, 0.66 mmol) in ethanol (12 mL) was added hydrazine hydrate (50%) (0.4 mL, 6.6 mmol) and an excess of Raney nickel slurry in water (1 mmol) was added slowly. The reaction was stirred at 70° C. for 1 hr. After 1 hr, the bubbling ceased, and the mixture was cooled to room temperature and filtered through Celite. The filtrate was condensed under reduced pressured and the residue was washed with $H_2O$/MeOH to afford the desired product 30 (2-(2-aminophenyl)-3-hydroxy-6,7-dimethoxyquinolin-4(1H)-one) (0.19 g, 93%).

A-5. Synthesis of Compounds 32 and 33

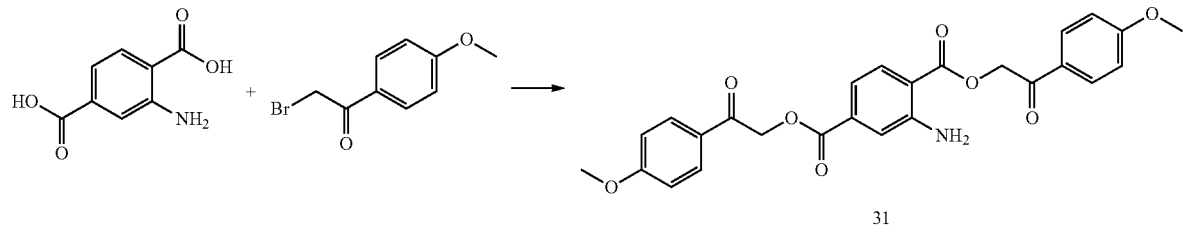

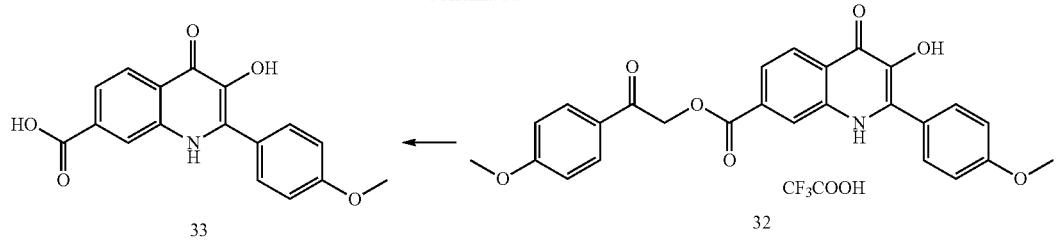

Step 1: Preparation of bis(2-(4-methoxyphenyl)-2-oxoethyl) 2-aminoterephthalate

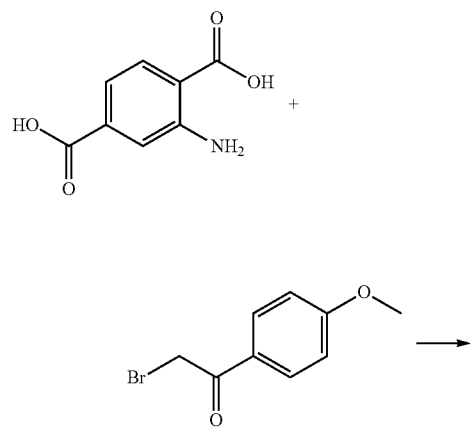

To the solution of 2-Aminoterephthalic acid (0.91 g, 5 mmol) in DMF (20 mL) was added potassium carbonate (1.38 g, 10 mmol) and p-methoxy-2-bromoacetophenone (2.4 g, 10.5 mmol). The reaction mixture was heated at 50° C. and stirred for 18 hr. Then the content of the flask was then poured into a 100 g mixture of water and ice. The precipitated solid material was collected by filtration, washed with water and methanol to afford Compound 31 (bis(2-(4-methoxyphenyl)-2-oxoethyl) 2-aminoterephthalate) with a yield of 1.9 g (80%).

Step 2: Preparation of 2-(4-methoxyphenyl)-2-oxoethyl 3-hydroxy-2-(4-methoxyphenyl)-4-oxo-1,4-dihydroquinoline-7-carboxylate 2,2,2-trifluoroacetate

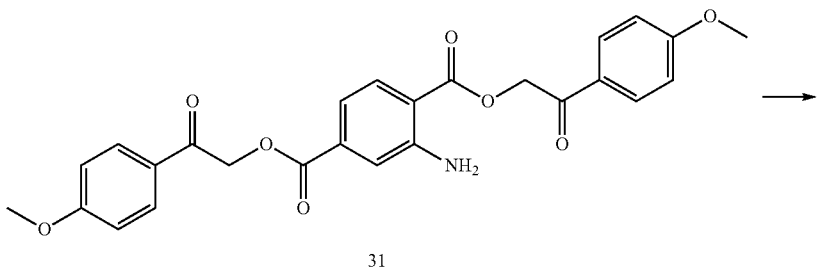

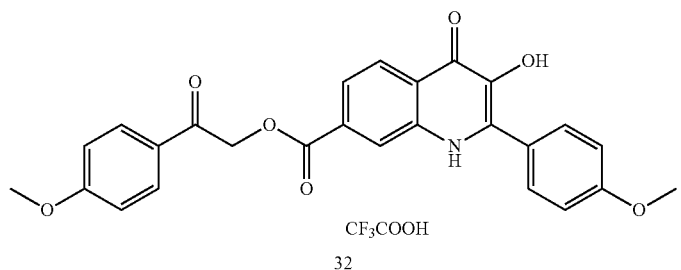

A solution of Compound 31 (0.5 g, 1.1 mmol) in TFA (12 mL) was heated to reflux for overnight, until reaction completed. Then the reaction mixture was cooled to room temperature, and TFA was removed in vacuo. The residue was added ice-water and stirred for 30 minutes. The solid was collected and washed by H₂O and methanol to obtain Compound 32 (2-(4-methoxyphenyl)-2-oxoethyl 3-hydroxy-2-(4-methoxyphenyl)-4-oxo-1,4-dihydroquinoline-7-carboxylate 2,2,2-trifluoroacetate) with a yield of 0.5 g (79%).

Step 3: Preparation of 3-hydroxy-2-(4-methoxyphenyl)-4-oxo-1,4-dihydroquinoline-7-carboxylic acid

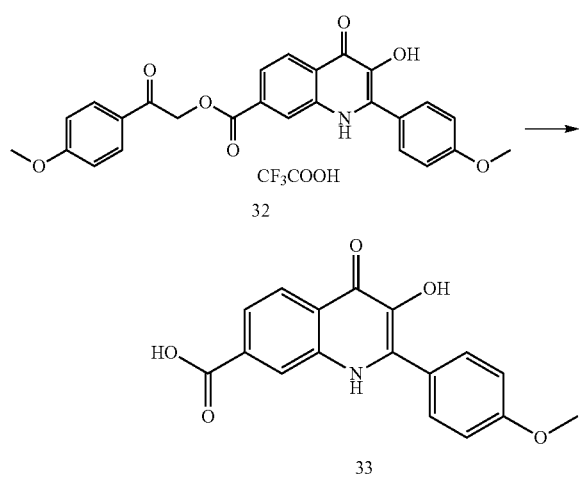

A solution of Compound 32 (0.1 g, 0.17 mmol) in THF (5 mL) was add 5 mL of 1N LiOH(aq) and stirred at room temperature for overnight, until reaction completed. The reaction mixture was then cooled to 0° C., and 2N HCl was added slowly until pH=1-2. The solid was collected and washed by H₂O and methanol to obtain Compound 33 (3-hydroxy-2-(4-methoxyphenyl)-4-oxo-1,4-dihydroquinoline-7-carboxylic acid) with a yield of 23 mg.

A-6. Synthesis of Compounds 34

Scheme VI

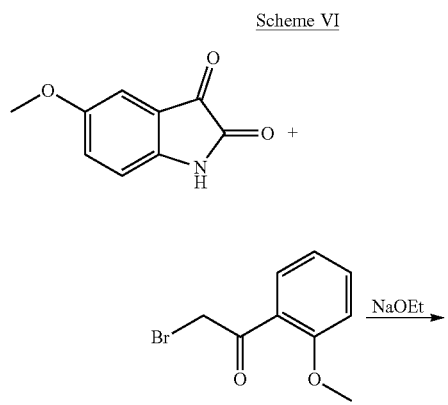

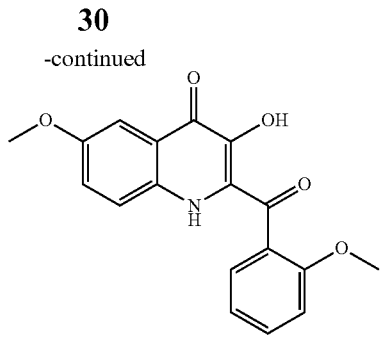

34

A solution of sodium ethoxide (Na, 2 mmol in dry EtOH, 5 mL) was add a suspension of 2,3-dihydro-2,3-dioxo-1H-indole (0.17 g, 1.0 mmol) and 2-bromo-2 methoxy acetophenone (0.23 g, 1.0 mmol) in dry EtOH (5 mL). The mixture was maintained at 0-5° C. for 2 hr. The reaction mixture was allowed to warm up to room temperature and stirred for 18 h. Then the mixture was acidified with 2N HCl(aq.) and extracted with EA. The organic phase was dried with MgSO₄ and concentrated under reduced pressure to give the crude mixture. The crude mixture was purified by column chromatography (EA/Hexanes=1/2) to give Compound 34 (3-hydroxy-6-methoxy-2-(2-methoxybenzoyl)quinolin-4(1H)-one) with a yield of 0.1 g (30%).

A-7. Synthesis of Compounds 35-38

Step 1: Preparation of 2-amino-1-(2-chlorophenyl)ethan-1-one hydrochloride

Scheme VII

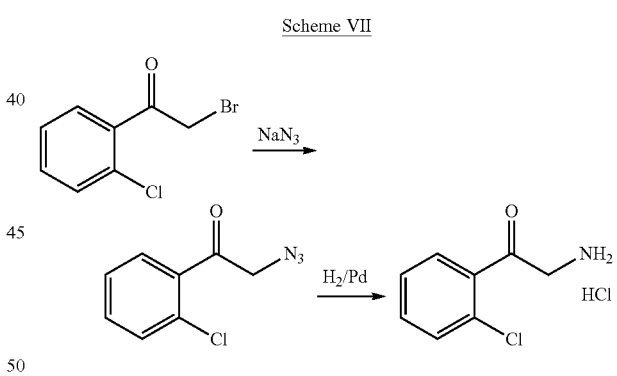

To the full dissolution of 2-bromo-1-(2-chlorophenyl)ethan-1-one (3.0 g, 12.85 mmol) in the DMSO was added sodium azide (1.2 g) and stirred at room temperature for 15 hr. The resulting mixture was diluted with H₂O. The layers are separated and extracted with EA. The combined organic layers are dried over MgSO₄, filtered and concentrated on a rotary evaporator to give the compound 2-azido-1-(2-chlorophenyl) ethan-1-one with a yield of 2.3 g (11.8 mmol).

A mixture of the 2-azido-1-(2-chlorophenyl)ethan-1-one (2.3 g, 11.8 mmol) and 5% Pd/C (0.5 g) in MeOH (100 mL) was added the concentrated HCl (2 mL) stirred under an atmosphere of H₂ (1 atm) at room temperature for 6 h. The mixture was filtered through celite and the filtrate was concentrated. The residue was not purified to provide the product. Compound 2-amino-1-(2-chlorophenyl) ethan-1-one hydrochloride with a yield of 2.2 g (10.73 mmol).

Step 2: Preparation of 2-(2-chlorophenyl)-7,8-dimethoxy-3,4-dihydro-5H-benzo[e][1,4] diazepin-5-one and 3-amino-2-(2-chlorophenyl)-6,7-dimethoxyquinolin-4(1H)-one

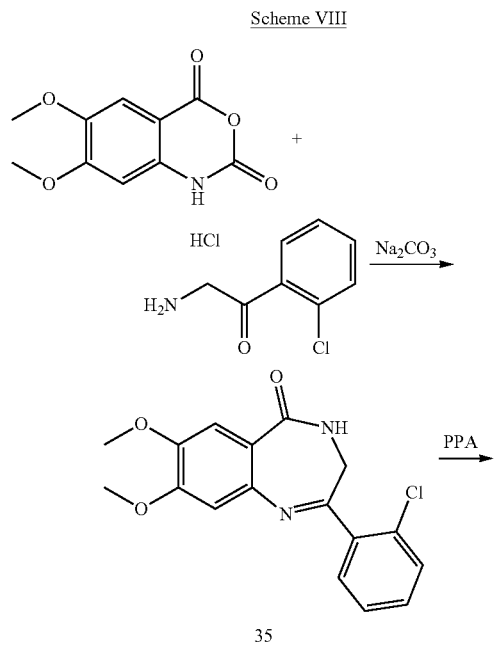

Scheme VIII

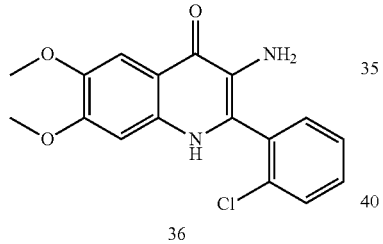

A mixture of the 2-amino-1-(2-chlorophenyl)ethan-1-one hydrochloride (1.0 g, 4.9 mmol), isatoic anhydride (0.9 g, 4.45 mmol), and Na$_2$CO$_3$ (0.6 g, 5.34 mmol) in H$_2$O (20 mL) was stirred at 80° C. for 4 hr. After the temperature cooled down to room temperature, the precipitate was collected by filtration and washed with H$_2$O and ether to give the Compound 35 (2-(2-chlorophenyl)-7,8-dimethoxy-3,4-dihydro-5H-benzo[e][1,4] diazepin-5-one) with a yield of 870.0 mg (2.64 mmol).

A mixture of the Compound 35 (2-(2-chlorophenyl)-7,8-dimethoxy-3,4-dihydro-5H-benzo[e][1,4] diazepin-5-one) (100.0 mg, 0.30 mmol) and PPA (5 mL) was stirred at 150° C. for 2 h. After the temperature cooled down to 0° C., the resulting mixture was poured onto Na$_2$CO$_{3(aq)}$, and after foaming had stopped, water was added. After 30 min of stirring, a solid product was filtered off and washed with water and methanol to give the Compound 36 (3-amino-2-(2-chlorophenyl)-6,7-dimethoxyquinolin-4(1H)-one) with a yield of 10.0 mg (0.03 mmol).

Similarly, Compounds 37-38 are synthesized by using the same methods as in Scheme VII and VIII.

A-8. Synthesis of Compound 39

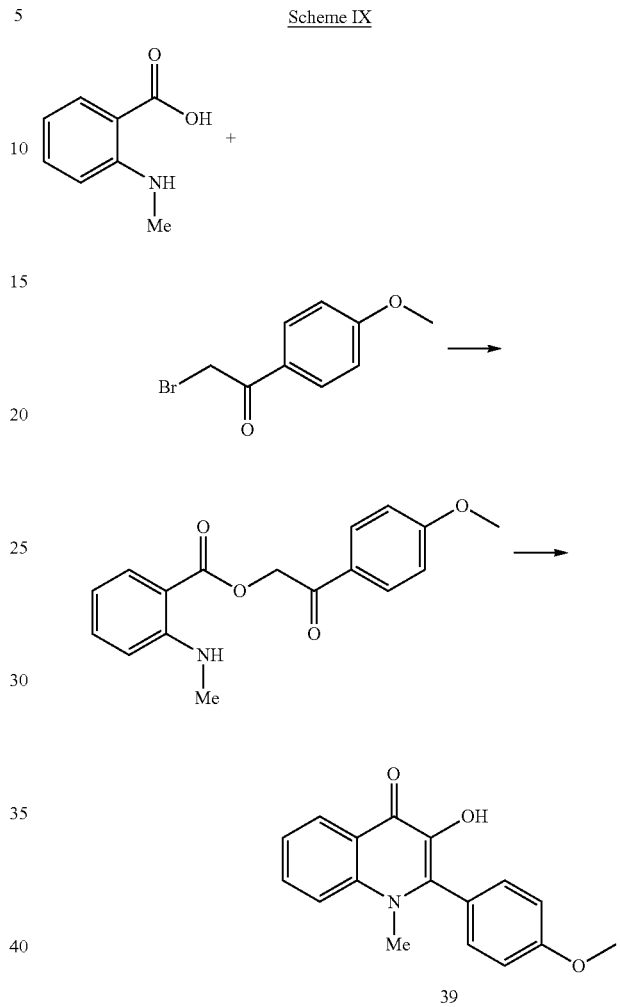

Compound 39 was synthesized by Scheme IX, which are using the methods similar to Scheme I.

A-9. Synthesis of Compound 40

Scheme X

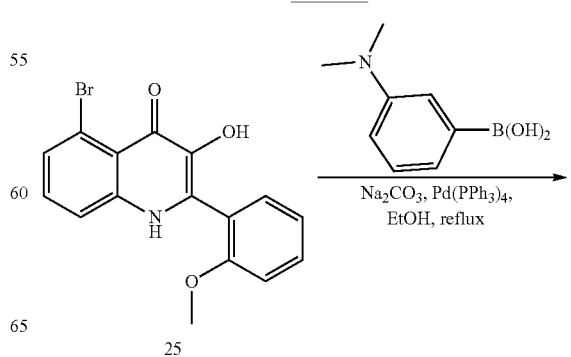

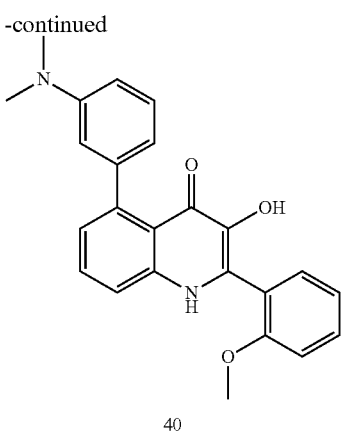

40

Compound 25 (0.3 g, 1.3 mmol) and 3-(N,N-dimethylamino)phenyl boronic acid (0.258 g, 1.56 mmol) were added into 3 ml ethanol, followed by adding sodium carbonate (1.1 g, 10.4 mmol) and tetrakis(triphenylphosphine)palladium(0) (0.075 g, 0.065 mmol). The reaction mixture was heated under reflux overnight. After cooling to room temperature, the residue was filtered. The filtrate was extracted with EA and dried in vacuo. The dried residue was then applied with column chromatography with EA: hexane (1:1) as eluent to obtain Compound 40 with a yield of 0.42 g (80%).

A-10. Synthesis of Compound 41-44

Step 1: Preparation of (3-hydroxy-6,7-dimethoxy-2-(2-(trifluoromethyl) phenyl) quinolin-4(1H)-one Scheme XI

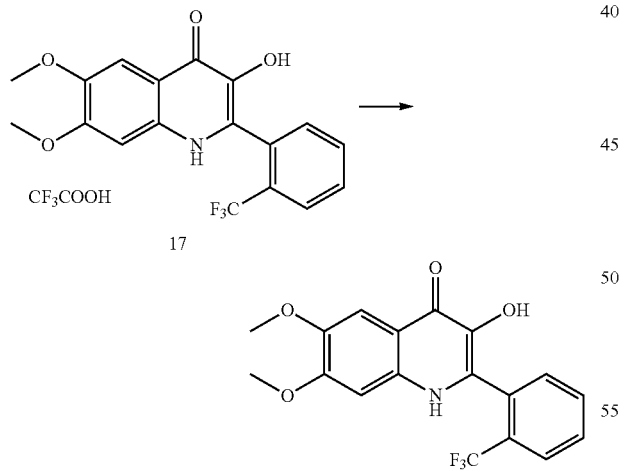

To the full dissolution of Compound 17 (30.0 mg, 0.06 mmol) in H₂O was added 1N NaOH (0.1 mL) stirred at room temperature for 3 hr. The precipitate was collected by filtration and washed with H₂O to give the free base Compound 41 (3-hydroxy-6,7-dimethoxy-2-(2-(trifluoromethyl)phenyl) quinolin-4(1H)-one) with a yield of 13.0 mg (0.04 mmol).

Step 2A: Preparation of 3-hydroxy-6,7-dimethoxy-2-(2-(trifluoromethyl)phenyl) quinolin-4(1H)-one hydrochloride Scheme XII

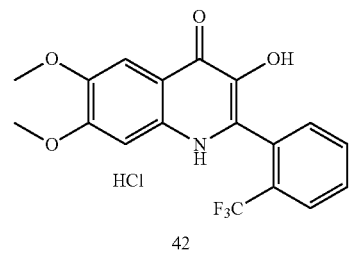

41

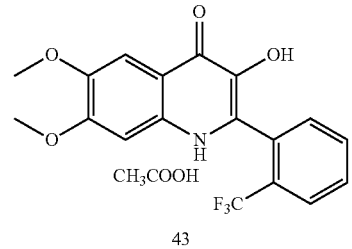

42

To the full dissolution of Compound 41 (0.29 g, 0.79 mmol) in the co-solvent of MeOH:DCM=2:1 was added 2N HCl in ether and stirred at room temperature for 3 hr. The precipitate was collected by filtration and washed with ether to give the Compound 42 (3-hydroxy-6,7-dimethoxy-2-(2-(trifluoromethyl)phenyl) quinolin-4(1H)-one hydrochloride) with a yield of 0.17 g (0.42 mmol).

Step 2B: Preparation of 3-hydroxy-6,7-dimethoxy-2-(2-(trifluoromethyl)phenyl)quinolin-4(1H)-one acetate

41

43

To the full dissolution of Compound 41 (3-hydroxy-6,7-dimethoxy-2-(2-(trifluoromethyl) phenyl) quinolin-4(1H)-one) (28.0 mg, 0.08 mmol) in the co-solvent of MeOH:DCM=2:1 was added acetic acid (0.01 mL) and stirred at 100° C. for 15 hr. The precipitate was collected by filtration and washed with ether to give the Compound 43 (3-hydroxy-6,7-dimethoxy-2-(2-(trifluoromethyl)phenyl)quinolin-4(1H)-one acetate) with a yield of 6.0 mg (0.014 mmol).

Step 2C: Preparation of 3-hydroxy-6,7-dimethoxy-2-(2-(trifluoromethyl)phenyl)quinolin-4(1H)-one methanesulfonate

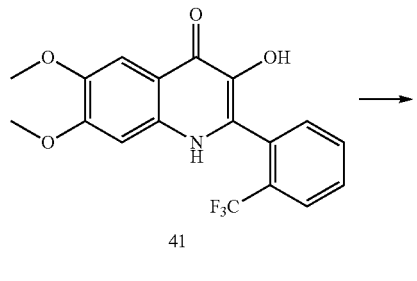

41

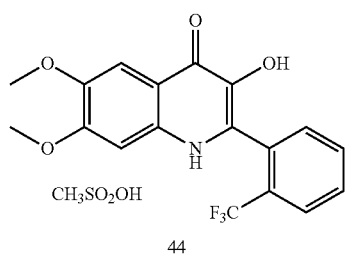

44

To the full dissolution of Compound 41 (3-hydroxy-6,7-dimethoxy-2-(2-(trifluoromethyl) phenyl)quinolin-4(1H)-one) (75.0 mg, 0.21 mmol) in the co-solvent of MeOH:DCM=2:1 was added methanesulfonic acid (16.3 μl) and stirred at room temperature for 15 hr. The precipitate was collected by filtration and washed with ether to give the Compound 44 (3-hydroxy-6,7-dimethoxy-2-(2-(trifluoromethyl)phenyl)quinolin-4(1H)-one methanesulfonate) with a yield of 21.0 mg (0.046 mmol).

A-11. Synthesis of Compounds 45-50

Compounds 45-50 were synthesized by using the methods as in Scheme XI.

A-12. Synthesis of Compound 51-52

Compounds 51-52 were synthesized by using the methods as in Scheme XII.

B. Pharmaceutically Acceptable Salts

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. In other particular embodiments, pharmaceutically acceptable salts are formed with malic acid. In particular embodiments, pharmaceutically acceptable salts are formed with hydrochloric acid. Active agents used to prepare compositions for the present disclosure may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

INDEX TABLE OF THE COMPOUNDS

| Cmpd. No. and Structure | $^1$H NMR Data |
| --- | --- |
| 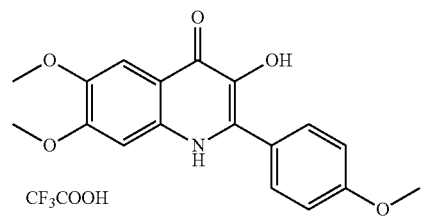<br>CF$_3$COOH<br>Chemical Formula: C$_{20}$H$_{18}$F$_3$NO$_7$<br>Exact Mass: 441.10<br>Molecular Weight: 441.36<br>Compound 2 | $^1$H-NMR (300 MHz, DMSO):<br>δ 11.25(s, 1H), 7.78-7.74(d, 2H), 7.41(s, 1H), 7.18(s, 1H), 7.13-7.09(d, 2H), 3.85(s, 6H), 3.84(s, 3H).<br>ESI-MS m/z calcd for C$_{20}$H$_{18}$F$_3$NO$_7$, 441.10 found 328.1[M + H]$^+$ |

-continued

INDEX TABLE OF THE COMPOUNDS

| Cmpd. No. and Structure | $^1$H NMR Data |
|---|---|
| 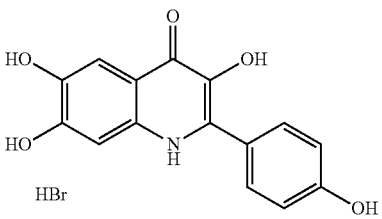 [SMILES: O=c1c(O)c(-c2ccc(O)cc2)[nH]c2cc(O)c(O)cc12 ; Br]<br>HBr<br>Chemical Formula: $C_{15}H_{12}BrNO_5$<br>Exact Mass: 364.99<br>Molecular Weight: 366.17<br>Compound 3 | $^1$H-NMR (400 MHz, DMSO): δ 7.72-7.70(d, 2H), 7.51(s, 1H), 7.30(s, 1H), 7.03-7.01(d, 2H).<br>ESI-MS m/z calcd for $C_{15}H_{12}BrNO_5$ 364.99, found 286.1[M + H]$^+$ |
| 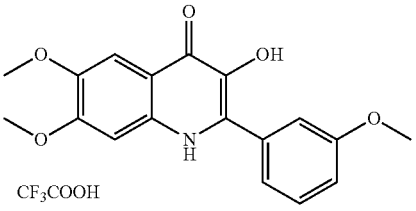<br>$CF_3COOH$<br>Chemical Formula: $C_{20}H_{18}F_3NO_7$<br>Exact Mass: 441.10<br>Molecular Weight: 441.36<br>Compound 4 | $^1$H-NMR (300 MHz, DMSO): δ 7.52-7.50(d, 1H), 7.47(s, 1H), 7.40(s, 1H), 7.38-7.36(m, 1H), 7.25(s, 1H), 7.13-7.10(dd, 1H), 3.89-3.84(m, 6H), 3.56(s, 3H).<br>ESI-MS m/z calcd for $C_{20}H_{18}F_3NO_7$ 441.10, found 328.3[M + H]$^+$ |
| 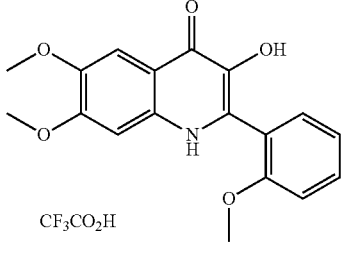 [SMILES: "CF3CO2H" ; COc1cc2[nH]c(-c3ccccc3OC)c(O)c(=O)c2cc1OC]<br>$CF_3CO_2H$<br>Chemical Formula: $C_{20}H_{18}F_3NO_7$<br>Exact Mass: 441.10<br>Molecular Weight: 441.36<br>Compound 5 | $^1$H-NMR (400 MHz, DMSO): δ 7.54-7.50(m, 1H), 7.46(s, 1H), 7.43-7.41(d, 1H), 7.22-7.20(d, 1H), 7.12-7.08(m, 1H), 7.07(s, 1H), 3.88(s, 3H), 3.85(s, 3H), 3.78(s, 3H).<br>ESI-MS m/z calcd for $C_{20}H_{18}F_3NO_7$ 441.10, found 328.3[M + H]$^+$ |
| 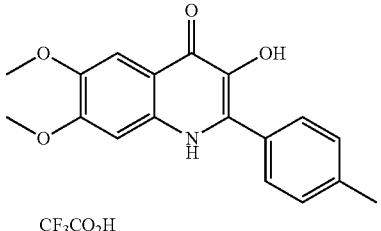<br>$CF_3CO_2H$<br>Chemical Formula: $C_{20}H_{18}F_3NO_6$<br>Exact Mass: 425.11<br>Molecular Weight: 425.36<br>Compound 6 | $^1$H-NMR (400 MHz, DMSO): δ 11.27(br, 1H), 7.71(d, 2H), 7.42(s, 1H), 7.36(d, 2H), 7.19(s, 1H), 3.86(s, 6H), 2.40(s, 3H).<br>ESI-MS m/z calcd for $C_{20}H_{18}F_3NO_6$ 425.11, found 312.3[M + H]$^+$ |

INDEX TABLE OF THE COMPOUNDS

| Cmpd. No. and Structure | ¹H NMR Data |
|---|---|
| 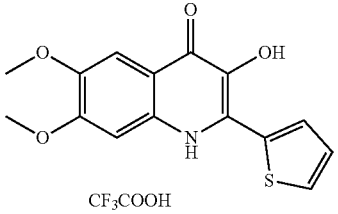 [SMILES: COc1cc2[nH]c(-c3cccs3)c(O)c(=O)c2cc1OC ; "CF3COOH"]<br>CF₃COOH<br>Chemical Formula: $C_{17}H_{14}F_3NO_6S$<br>Exact Mass: 417.05<br>Molecular Weight: 417.36<br>Compound 7 | ¹H-NMR (400 MHz, DMSO): δ 8.00(s, 1H), 7.87-7.85(m, 1H), 7.45(s, 1H), 7.33-7.29(m, 2H), 3.90(s, 3H), 3.84(s, 3H).<br>ESI-MS m/z calcd for $C_{17}H_{14}F_3NO_6S$ 417.05, found 304.2[M + H]⁺ |
| 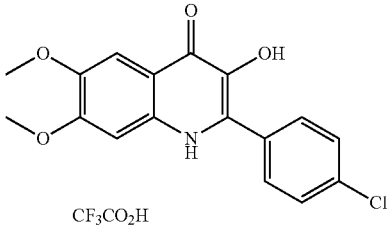 [SMILES: COc1cc2[nH]c(-c3ccc(Cl)cc3)c(O)c(=O)c2cc1OC ; "CF3CO2H"]<br>CF₃CO₂H<br>Chemical Formula: $C_{19}H_{15}ClF_3NO_6$<br>Exact Mass: 445.05<br>Molecular Weight: 445.78<br>Compound 8 | ¹H-NMR (400 MHz, DMSO): δ 7.85-7.82(d, 2H), 7.65-7.63(d, 2H), 7.46(s, 1H), 7.20(s, 1H), 3.87(s, 6H).<br>ESI-MS m/z calcd for $C_{19}H_{15}ClF_3NO_6$ 445.05, found 332.2[M + H]⁺ |
| 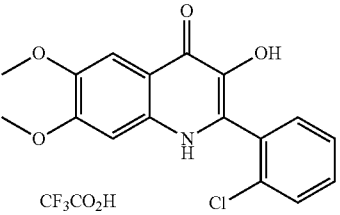<br>CF₃CO₂H<br>Chemical Formula: $C_{19}H_{15}ClF_3NO_6$<br>Exact Mass: 445.05<br>Molecular Weight: 445.78<br>Compound 9 | ¹H-NMR (400 MHz, DMSO): δ 7.66-7.48(m, 4H), 7.45(s, 1H), 6.98(s, 1H), 3.86(s, 3H), 3.83(s, 3H).<br>ESI-MS m/z calcd for $C_{19}H_{15}ClF_3NO_6$ 445.05, found 332.3[M + H]⁺ |
| 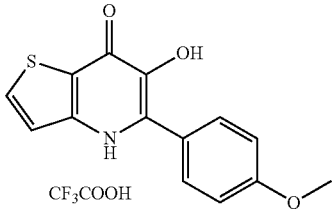 [SMILES: "CF3COOH" ; COc1ccc(-c2[nH]c3ccsc3c(=O)c2O)cc1]<br>CF₃COOH<br>Chemical Formula: $C_{16}H_{12}F_3NO_5S$<br>Exact Mass: 387.04<br>Molecular Weight: 387.33<br>Compound 10 | ¹H-NMR (300 MHz, DMSO): δ 7.92-7.90(d, 1H), 7.73-7.70(d, 2H), 7.24-7.22(d, 1H), 7.12-7.09(d, 2H), 3.83(s, 3H).<br>ESI-MS m/z calcd for $C_{16}H_{12}F_3NO_5S$ 387.04, found 274.2[M + H]⁺ |

-continued

INDEX TABLE OF THE COMPOUNDS

| Cmpd. No. and Structure | $^1$H NMR Data |
|---|---|
| 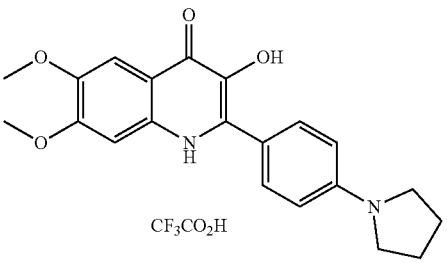 [SMILES: COc1cc2[nH]c(-c3ccc(N4CCCC4)cc3)c(O)c(=O)c2cc1OC ; "CF3CO2H"]<br>CF$_3$CO$_2$H<br>Chemical Formula: C$_{23}$H$_{23}$F$_3$N$_2$O$_6$<br>Exact Mass: 480.15<br>Molecular Weight: 480.44<br>Compound 11 | $^1$H-NMR (400 MHz, DMSO): δ 13.26(br, 1H), 7.78(d, 2H), 7.54(s, 1H), 7.49(s, 1H), 7.73(d, 2H), 3.93(s, 6H), 3.36-3.31(m, 4H), 2.02-1.91(m, 4H).<br>ESI-MS m/z calcd for C$_{23}$H$_{23}$F$_3$N$_2$O$_6$ 480.15, found 367.4[M + H]$^+$ |
| 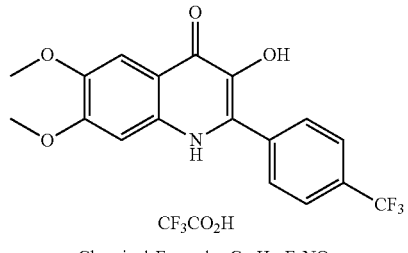<br>CF$_3$CO$_2$H<br>Chemical Formula: C$_{20}$H$_{15}$F$_6$NO$_6$<br>Exact Mass: 479.08<br>Molecular Weight: 479.33<br>Compound 12 | $^1$H-NMR (300 MHz, DMSO): δ 8.03(d, 2H), 7.93(d, 2H), 7.43(s, 1H), 7.15(s, 1H), 3.87(s, 6H).<br>ESI-MS m/z calcd for C$_{20}$H$_{15}$F$_6$NO$_6$ 479.08, found 366.3[M + H]$^+$ |
| 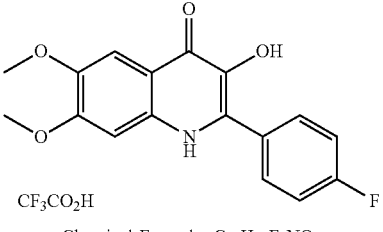<br>CF$_3$CO$_2$H<br>Chemical Formula: C$_{19}$H$_{15}$F$_4$NO$_6$<br>Exact Mass: 429.08<br>Molecular Weight: 429.32<br>Compound 13 | $^1$H-NMR (300 MHz, DMSO): δ 7.88-7.84(m, 2H), 7.47-7.39(m, 3H), 7.21(s, 1H), 3.88(s, 6H).<br>ESI-MS m/z calcd for C$_{19}$H$_{15}$F$_4$NO$_6$ 429.08, found 316.3[M + H]$^+$ |
| 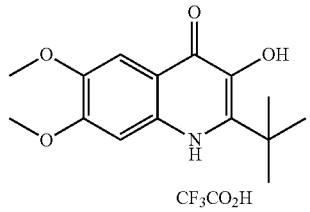 [SMILES: COc1cc2[nH]c(C(C)(C)C)c(O)c(=O)c2cc1OC ; "CF3CO2H"]<br>CF$_3$CO$_2$H<br>Chemical Formula: C$_{17}$H$_2$F$_3$NO$_6$<br>Exact Mass: 391.12<br>Molecular Weight: 391.34<br>Compound 14 | $^1$H-NMR (400 MHz, DMSO): δ 10.26(br, 1H), 7.55(s, 1H), 7.37(s, 1H), 3.86(s, 3H), 3.84(s, 3H), 1.48(s, 9H).<br>ESI-MS m/z calcd for C$_{17}$H$_{20}$F$_3$NO$_6$ 391.12, found 278.3[M + H]$^+$ |

INDEX TABLE OF THE COMPOUNDS

| Cmpd. No. and Structure | ¹H NMR Data |
|---|---|
| 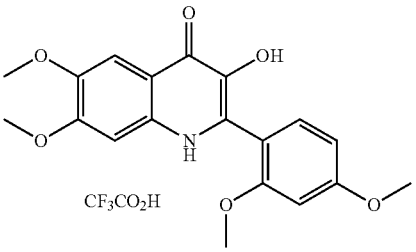<br>Chemical Formula: $C_{21}H_{20}F_3NO_8$<br>Exact Mass: 471.11<br>Molecular Weight: 471.39<br>Compound 15 | ¹H-NMR (300 MHz, DMSO): δ 7.41(s, 1H), 7.33-7.30(d, 1H), 7.01(s, 1H), 6.73(s, 1H), 6.67-6.64(d, 1H), 3.85-3.84(s, 6H), 3.82(s, 3H), 3.76(s, 3H).<br>ESI-MS m/z calcd for $C_{21}H_{20}F_3NO_8$ 471.11, found 358.3$[M + H]^+$ |
| 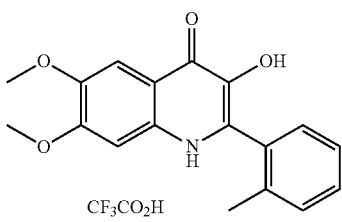<br>Chemical Formula: $C_{20}H_{18}F_3NO_6$<br>Exact Mass: 425.11<br>Molecular Weight: 425.36<br>Compound 16 | ¹H-NMR (300 MHz, DMSO): δ 11.43(s, 1H), 7.97(br, 1H), 7.44(s, 1H), 7.41-7.30(m, 4H), 7.02(s, 1H), 3.86(s, 3H), 3.82(s, 3H), 2.22(s, 3H).<br>ESI-MS m/z calcd for $C_{20}H_{18}F_3NO_6$ 425.11, found 312.3$[M + H]^+$ |
| 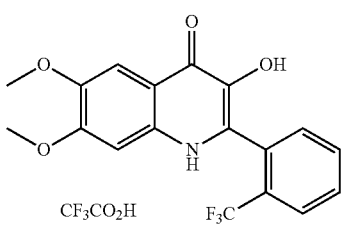 [SMILES: COc1cc2[nH]c(-c3ccccc3C(F)(F)F)c(O)c(=O)c2cc1OC ; "CF3CO2H"]<br>Chemical Formula: $C_{20}H_{15}F_6NO_6$<br>Exact Mass: 479.08<br>Molecular Weight: 479.33<br>Compound 17 | ¹H-NMR (400 MHz, DMSO): δ 8.02-7.99(d, 1H), 7.94-7.74(m, 2H), 7.62-7.60(d, 1H), 7.45(s, 1H), 6.94(s, 1H), 3.94(s, 3H), 3.86(s, 3H).<br>ESI-MS m/z calcd for $C_{20}H_{15}F_6NO_6$ 479.08, found 366.3$[M + H]^+$ |
| 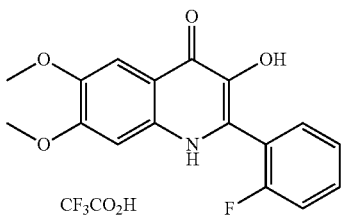 [SMILES: COc1cc2[nH]c(-c3ccccc3F)c(O)c(=O)c2cc1OC ; "CF3CO2H"]<br>Chemical Formula: $C_{19}H_{15}F_4NO_6$<br>Exact Mass: 429.08<br>Molecular Weight: 429.32<br>Compound 18 | ¹H-NMR (400 MHz, DMSO): δ 7.61-7.53(m, 2H), 7.42(s, 1H), 7.40-7.33(m, 2H), 6.99(s, 1H), 3.84(s, 3H), 3.82(s, 3H).<br>ESI-MS m/z calcd for $C_{19}H_{15}F_4NO_6$ 429.08, found 316.3$[M + H]^+$ |

INDEX TABLE OF THE COMPOUNDS

| Cmpd. No. and Structure | $^1$H NMR Data |
|---|---|
| 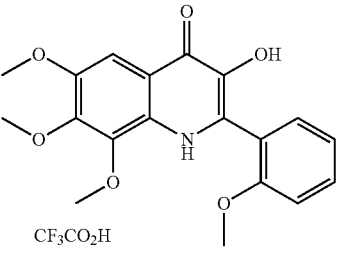 [SMILES: "CF3CO2H" ; COc1ccccc1-c1[nH]c2c(OC)c(OC)c(OC)cc2c(=O)c1O]<br>CF$_3$CO$_2$H<br>Chemical Formula: C$_{21}$H$_{20}$F$_3$NO$_8$<br>Exact Mass: 471.11<br>Molecular Weight: 471.39<br>Compound 19 | $^1$H-NMR (400 MHz, DMSO): δ 7.49-7.41(m, 2H), 7.31(s, 1H), 7.17-7.04(m, 2H), 3.90-3.87(m, 9H), 3.76(s, 3H).<br>ESI-MS m/z calcd for C$_{21}$H$_{20}$F$_3$NO$_8$ 471.11, found 358.3[M + H]$^+$ |
| 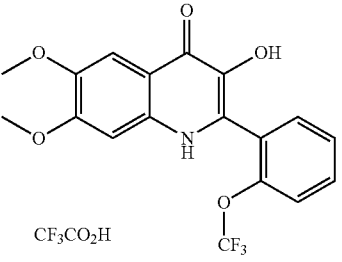 [SMILES: "CF3CO2H" ; COc1cc2[nH]c(-c3ccccc3OC(F)(F)F)c(O)c(=O)c2cc1OC]<br>CF$_3$CO$_2$H<br>Chemical Formula: C$_{20}$H$_{15}$F$_6$NO$_7$<br>Exact Mass: 495.08<br>Molecular Weight: 495.33<br>Compound 20 | $^1$H-NMR (300 MHz, DMSO): δ 7.69-7.65(m, 2H), 7.59-7.54(m, 2H), 7.44(s, 1H), 7.00(s, 1H), 3.86(s, 3H), 3.84(s, 3H).<br>ESI-MS m/z calcd for C$_{20}$H$_{15}$F$_6$NO$_7$ 495.08, found 382.3[M + H]$^+$ |
| 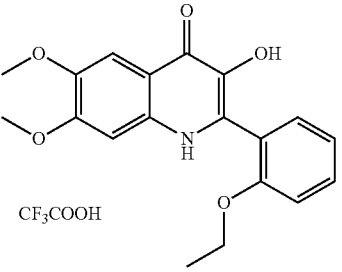 [SMILES: "CF3COOH" ; CCOc1ccccc1-c1[nH]c2cc(OC)c(OC)cc2c(=O)c1O]<br>CF$_3$COOH<br>Chemical Formula: C$_{21}$H$_{20}$F$_3$NO$_7$<br>Exact Mass: 455.12<br>Molecular Weight: 455.39<br>Compound 21 | $^1$H-NMR (300 MHz, DMSO): δ 7.65-7.57(m, 1H), 7.50-7.42(m, 2H), 7.20-7.14(m, 1H), 7.10-7.00(m, 2H), 4.40-4.33(q, 2H), 3.86(s, 3H), 3.83(s, 3H), 1.23-1.19(t, 3H).<br>ESI-MS m/z calcd for C$_{21}$H$_{20}$F$_3$NO$_7$ 455.12, found 342.3[M + H]$^+$ |
| 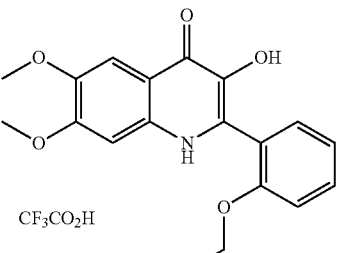<br>CF$_3$CO$_2$H<br>Chemical Formula: C$_{22}$H$_{22}$F$_3$NO$_7$<br>Exact Mass: 469.13<br>Molecular Weight: 469.41<br>Compound 22 | $^1$H-NMR (400 MHz, DMSO): δ 7.47-7.40(m, 3H), 7.18-7.16(d, 1H), 7.08-7.04(m, 1H), 7.00(s, 1H), 3.97-3.94(t, 2H), 3.85(s, 3H), 3.81(s, 3H), 1.62-1.56(m, 2H), 0.84-0.80(t, 3H).<br>ESI-MS m/z calcd for C$_{22}$H$_{22}$F$_3$NO$_7$ 469.13, found 356.3[M + H]$^+$ |

INDEX TABLE OF THE COMPOUNDS

| Cmpd. No. and Structure | ¹H NMR Data |
|---|---|
| 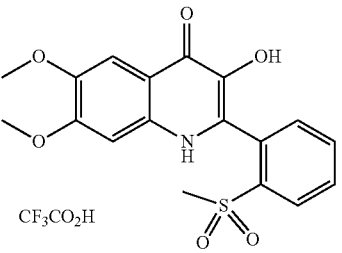 [SMILES: "CF3CO2H" ; COc1cc2[nH]c(-c3ccccc3S(C)(=O)=O)c(O)c(=O)c2cc1OC]<br>Chemical Formula: $C_{20}H_{18}F_3NO_8S$<br>Exact Mass: 489.07<br>Molecular Weight: 489.42<br>Compound 23 | ¹H-NMR (400 MHz, DMSO): δ 12.11(br, 1H), 8.13(dd, 1H), 7.91-7.82(m, 2H), 7.62(dd, 1H), 7.48(s, 1H), 6.98(s, 1H), 3.88(s, 3H), 3.83(s, 3H), 3.17(s, 3H).<br>ESI-MS m/z calcd for $C_{20}H_{18}F_3NO_8S$ 489.07, found 376.3[M + H]⁺ |
| 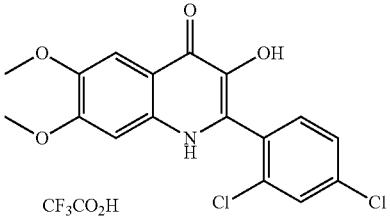 [SMILES: "CF3CO2H" ; COc1cc2[nH]c(-c3ccc(Cl)cc3Cl)c(O)c(=O)c2cc1OC]<br>Chemical Formula: $C_{19}H_{14}Cl_2F_3NO_6$<br>Exact Mass: 479.02<br>Molecular Weight: 480.22<br>Compound 24 | ¹H-NMR (300 MHz, DMSO): δ 7.85(s, 1H), 7.60(s, 2H), 7.44(s, 1H), 6.95(s, 1H), 3.90(s, 3H), 3.84(s, 3H).<br>ESI-MS m/z calcd for $C_{19}H_{14}Cl_2F_3NO_6$ 479.02, found 366.2[M + H]⁺ |
| 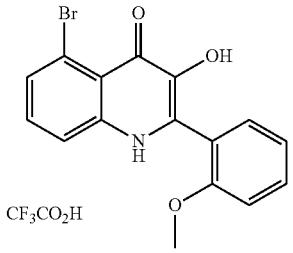 [SMILES: "CF3CO2H" ; COc1ccccc1-c1[nH]c2cccc(Br)c2c(=O)c1O]<br>Chemical Formula: $C_{18}H_{13}BrF_3NO_5$<br>Exact Mass: 458.99<br>Molecular Weight: 460.20<br>Compound 25 | ¹H-NMR (400 MHz, DMSO): δ 7.59-7.57(d, 1H), 7.54-7.49(m, 1H), 7.46-7.41(m, 2H), 7.38-7.34(m, 1H), 7.22-7.19(d, 1H), 7.11-7.08(m, 1H), 3.77(s, 3H).<br>ESI-MS m/z calcd for $C_{18}H_{13}BrF_3NO_5$ 458.99, found 346.2[M + H]⁺ |
| 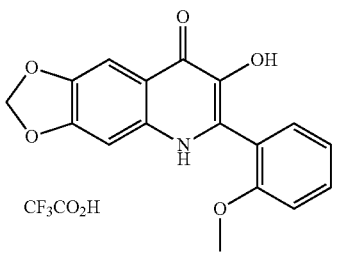 [SMILES: "CF3CO2H" ; COc1ccccc1-c1[nH]c2cc3c(cc2c(=O)c1O)OCO3]<br>Chemical Formula: $C_{19}H_{14}F_3NO_7$<br>Exact Mass: 425.07<br>Molecular Weight: 425.32<br>Compound 26 | ¹H-NMR (300 MHz, DMSO): δ 7.52-7.47(m, 1H), 7.41-7.39(m, 2H), 7.21-7.18(d, 1H), 7.14-7.06(m, 1H), 6.98(s, 1H), 6.13(s, 2H), 3.77(s, 3H).<br>ESI-MS m/z calcd for $C_{19}H_{14}F_3NO_7$ 425.07, found 312.2[M + H]⁺ |

INDEX TABLE OF THE COMPOUNDS

| Cmpd. No. and Structure | ¹H NMR Data |
|---|---|
| 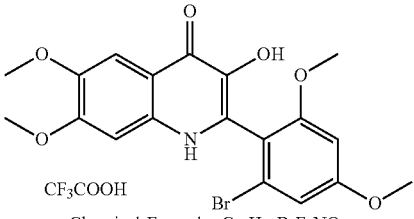<br>CF₃COOH<br>Chemical Formula: $C_{21}H_{19}BrF_3NO_8$<br>Exact Mass: 549.02<br>Molecular Weight: 550.28<br>Compound 27 | ¹H-NMR (300 MHz, CD3OD): δ 7.72(s, 1H), 7.57(s, 1H), 7.16(s, 1H), 6.90(s, 1H), 4.03(s, 3H), 4.02-4.00(m, 6H), 3.92(s, 3H).<br>ESI-MS m/z calcd for $C_{21}H_{19}BrF_3NO_8$ 549.02, found 436.2[M + H] |
| 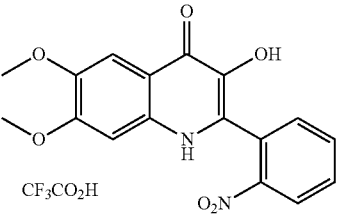 [SMILES: "CF3CO2H" ; COc1cc2[nH]c(-c3ccccc3[N+](=O)[O-])c(O)c(=O)c2cc1OC]<br>CF₃CO₂H<br>Chemical Formula: $C_{19}H_{15}F_3N_2O_8$<br>Exact Mass: 456.08<br>Molecular Weight: 456.33<br>Compound 29 | ¹H-NMR (400 MHz, DMSO): δ 11.78(br, 1H), 8.16(d, 1H), 7.92(d, 1H), 7.89-7.74(m, 2H), 7.44(s, 1H), 7.00(s, 1H), 3.86(s, 6H).<br>ESI-MS m/z calcd for $C_{19}H_{15}F_3N_2O_8$ 456.08, found 343.3[M + H]⁺ |
| 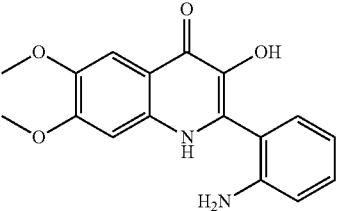<br>Chemical Formula: $C_{17}H_{16}N_2O_4$<br>Exact Mass: 312.11<br>Molecular Weight: 312.33<br>Compound 30 | ¹H-NMR (400 MHz, DMSO): δ 11.29(br, 1H), 7.43(s, 1H), 7.21(d, 2H), 7.09(s, 1H), 6.82(d, 1H), 6.71(m, 2H), 4.96(br, 2H), 3.92(s, 3H), 3.85(s, 3H).<br>ESI-MS m/z calcd for $C_{17}H_{16}N_2O_4$ 312.11, found 313.3[M + H]⁺ |
| 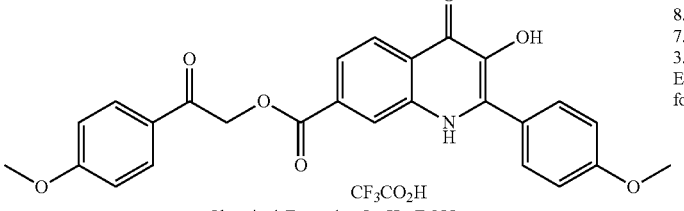<br>CF₃CO₂H<br>Chemical Formula: $C_{28}H_{22}F_3NO_9$<br>Exact Mass: 573.12<br>Molecular Weight: 573.48<br>Compound 32 | ¹H-NMR (300 MHz, DMSO): δ 8.55(s, 1H), 8.30-8.27(d, 1H), 8.03-8.00(d, 2H), 7.85-7.79(m, 3H), 7.16-7.10(m, 4H), 5.76(s, 2H), 3.90(s, 3H), 3.87(s, 3H).<br>ESI-MS m/z calcd for $C_{28}H_{22}F_3NO_9$ 573.12, found 460.4[M + H]⁺ |
| 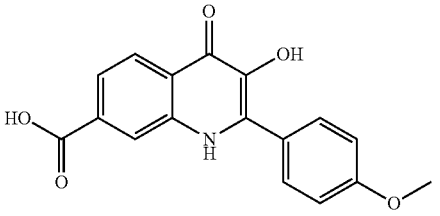<br>Chemical Formula: $C_{17}H_{13}NO_5$<br>Exact Mass: 311.08<br>Molecular Weight: 311.29<br>Compound 33 | ¹H-NMR (300 MHz, DMSO): δ 8.41(s, 1H), 8.23-8.20(d, 1H), 7.81-7.78(d, 2H), 7.75-7.72(d, 1H), 7.15-7.12(d, 2H), 3.84(s, 3H).<br>ESI-MS m/z calcd for $C_{17}H_{13}NO_5$ 311.08, found 312.3[M + H]⁺ |

INDEX TABLE OF THE COMPOUNDS

| Cmpd. No. and Structure | ¹H NMR Data |
|---|---|
| 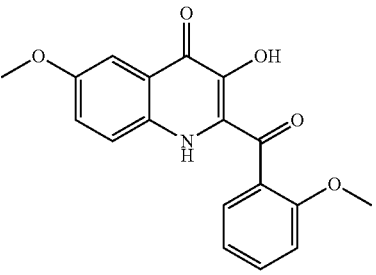<br>Chemical Formula: $C_{18}H_{15}NO_5$<br>Exact Mass: 325.10<br>Molecular Weight: 325.32<br>Compound 34 | ¹H-NMR (400 MHz, CDCl3): δ 7.94-7.93(d, 1H), 7.54-7.50(m, 1H), 7.07-7.03(m, 1H), 6.91-6.89(d, 1H), 6.87-6.81(m, 3H), 3.82(s, 3H), 3.78(s, 3H).<br>ESI-MS m/z calcd for $C_{18}H_{15}NO_5$ 325.10, found 348.3[M + Na] |
| 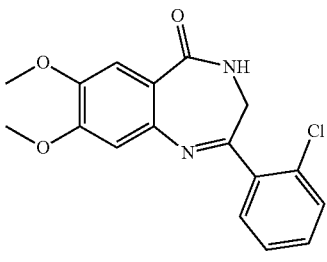 [SMILES: COc1cc2c(cc1OC)C(=O)NCC(c1ccccc1Cl)=N2]<br>Chemical Formula: $C_{17}H_{15}ClN_2O_3$<br>Exact Mass: 330.08<br>Molecular Weight: 330.77<br>Compound 35 | ¹H-NMR (400 MHz, CDCl$_3$): δ 7.63-7.60(dd, 1H), 7.52(s, 1H), 7.49-7.45(m, 1H), 7.44-7.36(m, 2H), 6.93(s, 1H), 4.08-4.06(d, 2H), 4.00(s, 3H), 3.96(s, 3H).<br>ESI-MS m/z calcd for $C_{17}H_{15}ClN_2O_3$ 330.08, found 331.1[M + H]⁺ |
| 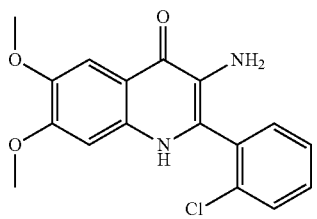 [SMILES: COc1cc2[nH]c(-c3ccccc3Cl)c(N)c(=O)c2cc1OC]<br>Chemical Formula: $C_{17}H_{15}ClN_2O_3$<br>Exact Mass: 330.08<br>Molecular Weight: 330.77<br>Compound 36 | ¹H-NMR (400 MHz, CD3OD): δ 7.67-7.65(d, 1H), 7.61-7.52(m, 4H), 7.02(s, 1H), 3.95(s, 3H), 3.92(s, 3H).<br>ESI-MS m/z calcd for $C_{17}H_{15}ClN_2O_3$ 330.08, found 331.1[M+H]⁺ |
| 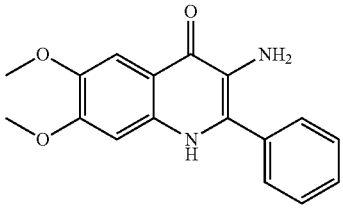 [SMILES: COc1cc2[nH]c(-c3ccccc3)c(N)c(=O)c2cc1OC]<br>Chemical Formula: $C_{17}H_{16}Cl_2N_2O_3$<br>Exact Mass: 296.12<br>Molecular Weight: 296.33<br>Compound 37 | ¹H-NMR (300 MHz, DMSO): δ 7.70-7.64(d, 2H), 7.58-7.46(m, 3H), 7.41(s, 1H), 7.10(s, 1H), 4.16(br, 2H), 3.96(s, 3H), 3.82(s, 3H).<br>ESI-MS m/z calcd for $C_{17}H_{16}Cl_2N_2O_3$ 296.12, found 297.3[M + H]⁺ |

INDEX TABLE OF THE COMPOUNDS

| Cmpd. No. and Structure | ¹H NMR Data |
|---|---|
| 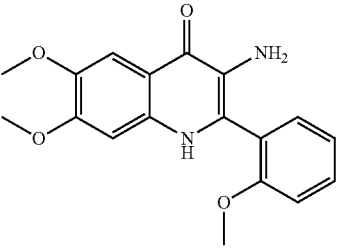 [SMILES: COc1cc2[nH]c(-c3ccccc3OC)c(N)c(=O)c2cc1OC]<br>Chemical Formula: $C_{18}H_{18}N_2O_4$<br>Exact Mass: 326.13<br>Molecular Weight: 326.35<br>Compound 38 | ¹H-NMR (300 MHz, DMSO): δ 8.40-8.36(m, 2H), 7.58-7.56(d, 1H), 7.53-7.48(dd, 1H), 7.33(s, 1H), 7.18-7.15(d, 1H), 7.07-7.02(dd, 1H), 6.90(s, 1H), 3.94(s, 3H), 3.84-3.81(m, 6H).<br>ESI-MS m/z calcd for $C_{18}H_{18}N_2O_4$ 326.13, found 327.3[M+H]⁺ |
| 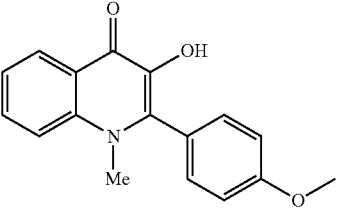 [SMILES: COc1ccc(-c2c(O)c(=O)c3ccccc3n2C)cc1]<br>Chemical Formula: $C_{17}H_{15}NO_3$<br>Exact Mass: 281.1052<br>Molecular Weight: 281.3110<br>Compound 39 | ¹H-NMR (300 MHz, DMSO): δ 8.31-8.28(d, 1H), 8.09-7.78(m, 1H), 7.76-7.69(m, 2H), 7.40-7.35(d, 2H), 7.12-7.09(d, 2H), 3.84(s, 3H), 3.55(s, 3H).<br>ESI-MS m/z calcd for $C_{17}H_{15}NO_3$ 281.11, found 282.3[M + H]⁺ |
| 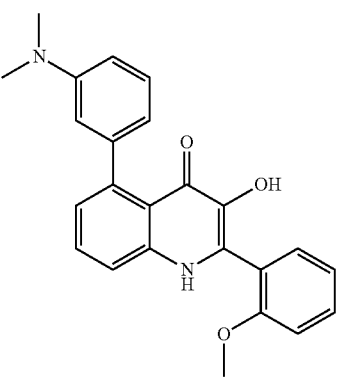 [SMILES: COc1ccccc1-c1[nH]c2cccc(-c3cccc(N(C)C)c3)c2c(=O)c1O]<br>Chemical Formula: $C_{24}H_{22}N_2O_3$<br>Exact Mass: 386.16<br>Molecular Weight: 386.45<br>Compound 40 | ¹H-NMR (300 MHz, CDCl₃): δ 7.97-7.94(d, 1H), 7.56-7.33(m, 4H), 7.15-7.04(m, 6H), 3.94(s, 3H), 3.07(s, 6H).<br>ESI-MS m/z calcd for $C_{24}H_{22}N_2O_3$ 386.16, found 387.4[M + H]⁺ |
| 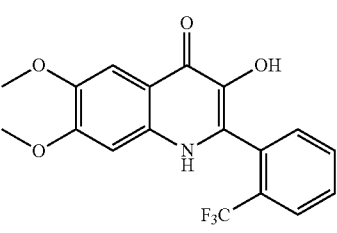<br>Chemical Formula: $C_{18}H_{14}F_3NO_4$<br>Exact Mass: 365.09<br>Molecular Weight: 365.31<br>Compound 41 | ¹H-NMR (300 MHz, DMSO): δ 7.98-7.96(d, 1H), 7.90-7.79(m, 2H), 7.69-7.67(d, 1H), 7.56(s, 1H), 7.09(s, 1H), 3.91(s, 3H), 3.80(s, 3H). ¹⁹F-NMR (300 MHz, DMSO): δ -58.54.<br>ESI-MS m/z calcd for $C_{18}H_{14}F_3NO_4$ 365.09, found 366.3[M + H]⁺ |

INDEX TABLE OF THE COMPOUNDS

| Cmpd. No. and Structure | $^1$H NMR Data |
|---|---|
| 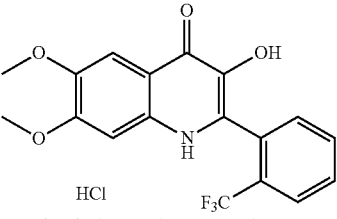 [SMILES: COc1cc2[nH]c(-c3ccccc3C(F)(F)F)c(O)c(=O)c2cc1OC ; Cl]<br>HCl<br>Chemical Formula: $C_{18}H_{15}ClF_3NO_4$<br>Exact Mass: 401.06<br>Molecular Weight: 401.77<br>Compound 42 | $^1$H-NMR (300 MHz, DMSO): δ 8.00-7.98(d, 1H), 7.92-7.81(m, 2H), 7.73-7.71(d, 1H), 7.68(s, 1H), 7.23(s, 1H), 3.94(s, 3H), 3.90(s, 3H). $^{19}$F-NMR (300 MHz, DMSO): δ −58.49. ESI-MS m/z calcd for $C_{18}H_{15}ClF_3NO_4$ 401.06, found 366.3[M + H]$^+$ |
| 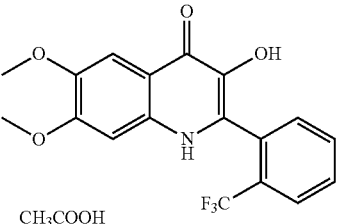<br>CH$_3$COOH<br>Chemical Formula: $C_{20}H_{18}F_3NO_6$<br>Exact Mass: 425.11<br>Molecular Weight: 425.36<br>Compound 43 | $^1$H-NMR (400 MHz, DMSO): δ 7.94-7.92(d, 1H), 7.85-7.78(m, 2H), 7.76-7.60(d, 1H), 7.44(s, 1H), 6.99(s, 1H), 3.86(s, 3H), 3.83(s, 3H). $^{19}$F-NMR (400 MHz, DMSO): δ −58.63. ESI-MS m/z calcd for $C_{20}H_{18}F_3NO_6$ 425.11, found 366.3[M + H]$^+$ |
| 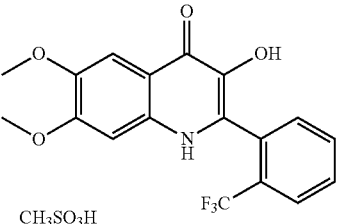<br>CH$_3$SO$_3$H<br>Chemical Formula: $C_{19}H_{18}F_3NO_7S$<br>Exact Mass: 461.08<br>Molecular Weight: 461.41<br>Compound 44 | $^1$H-NMR (400 MHz, DMSO): δ 7.98-7.96(d, 1H), 7.89-7.79(m, 2H), 7.69-7.67(d, 1H), 7.56(s, 1H), 7.09(s, 1H), 3.93(s, 3H), 3.87(s, 3H). $^{19}$F-NMR (400 MHz, DMSO): δ −58.54. ESI-MS m/z calcd for $C_{19}H_{18}F_3NO_7S$ 461.08, found 366.3[M + H]$^+$ |
| 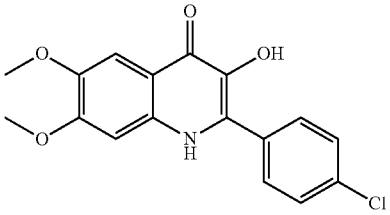 [SMILES: COc1cc2[nH]c(-c3ccc(Cl)cc3)c(O)c(=O)c2cc1OC]<br>Chemical Formula: $C_{17}H_{14}ClNO_4$<br>Exact Mass: 331.06<br>Molecular Weight: 331.75<br>Compound 45 | $^1$H-NMR (400 MHz, DMSO): δ 7.88-7.86(d, 2H), 7.61-7.59(d, 2H), 7.41(s, 1H), 7.13(s, 1H), 3.85(s, 6H).<br>ESI-MS m/z calcd for $C_{17}H_{14}ClNO_4$ 331.06, found 332.2[M + H]$^+$ |
| 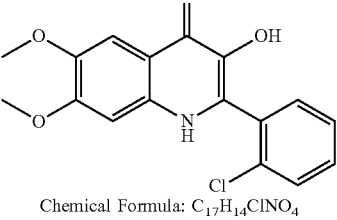<br>Chemical Formula: $C_{17}H_{14}ClNO_4$<br>Exact Mass: 331.06<br>Molecular Weight: 331.75<br>Compound 46 | $^1$H-NMR (400 MHz, DMSO): δ 7.64-7.48(m, 4H), 7.44(s, 1H), 6.97(s, 1H), 3.85(s, 3H), 3.82(s, 3H).<br>ESI-MS m/z calcd for $C_{17}H_{14}ClNO_4$ 331.06, found 332.3[M + H]$^+$ |

-continued

INDEX TABLE OF THE COMPOUNDS

| Cmpd. No. and Structure | ¹H NMR Data |
|---|---|
| 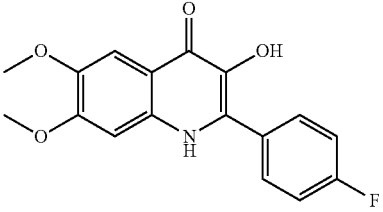 [SMILES: COc1cc2[nH]c(-c3ccc(F)cc3)c(O)c(=O)c2cc1OC]<br>Chemical Formula: $C_{17}H_{14}FNO_4$<br>Exact Mass: 315.09<br>Molecular Weight: 315.30<br>Compound 47 | ¹H-NMR (400 MHz, DMSO): δ 7.86-7.82(m, 2H), 7.43-7.37(m, 3H), 7.15(s, 1H), 3.85(s, 6H).<br>ESI-MS m/z calcd for $C_{17}H_{14}FNO_4$ 315.09, found 316.3[M + H]⁺ |
| 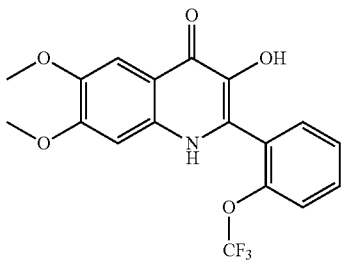 [SMILES: COc1cc2[nH]c(-c3ccccc3OC(F)(F)F)c(O)c(=O)c2cc1OC]<br>Chemical Formula: $C_{18}H_{14}F_3NO_5$<br>Exact Mass: 381.08<br>Molecular Weight: 381.31<br>Compound 48 | ¹H-NMR (300 MHz, DMSO): δ 7.67-7.65(d, 2H), 7.59-7.54(dd, 2H), 7.44(s, 1H), 6.99(s, 1H), 3.86(s, 3H), 3.84(s, 3H).<br>ESI-MS m/z calcd for $C_{18}H_{14}F_3NO_5$ 381.08, found 382.3[M + H]⁺ |
| 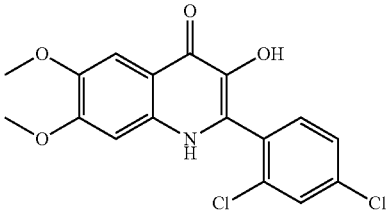 [SMILES: COc1cc2[nH]c(-c3ccc(Cl)cc3Cl)c(O)c(=O)c2cc1OC]<br>Chemical Formula: $C_{17}H_{13}Cl_2NO_4$<br>Exact Mass: 365.02<br>Molecular Weight: 366.19<br>Compound 49 | ¹H-NMR (400 MHz, DMSO): δ 7.84(s, 1H), 7.60(s, 2H), 7.44(s, 1H), 6.95(s, 1H), 3.85(s, 6H).<br>ESI-MS m/z calcd for $C_{17}H_{13}Cl_2NO_4$ 365.02, found 366.0[M + H]⁺ |
| 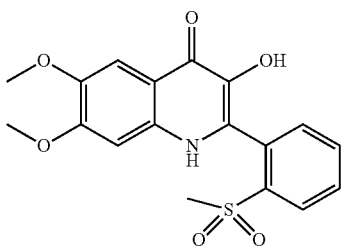 [SMILES: COc1cc2[nH]c(-c3ccccc3S(C)(=O)=O)c(O)c(=O)c2cc1OC]<br>Chemical Formula: $C_{18}H_{17}NO_6S$<br>Exact Mass: 375.08<br>Molecular Weight: 375.40<br>Compound 50 | ¹H-NMR (300 MHz, DMSO): δ 8.15(dd, 1H), 7.91-7.78(m, 2H), 7.59(dd, 1H), 7.42(s, 1H), 6.96(s, 1H), 3.84(s, 3H), 3.82(s, 3H), 3.18(s, 3H).<br>ESI-MS m/z calcd for $C_{18}H_{17}NO_6S$ 375.08, found 376.1[M + H]⁺ |

INDEX TABLE OF THE COMPOUNDS

| Cmpd. No. and Structure | $^1$H NMR Data |
|---|---|
| 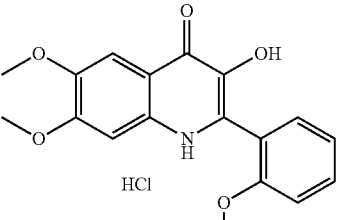<br>Chemical Formula: $C_{18}H_{18}ClNO_5$<br>Exact Mass: 363.09<br>Molecular Weight: 363.79<br>Compound 51 | 1H-NMR (300 MHz, DMSO): δ 7.58-7.55(d, 1H), 7.51(s, 1H), 7.47-7.44(d, 1H), 7.25-7.22(d, 1H), 7.16-7.09(m, 2H), 3.90(s, 3H), 3.86(s, 3H), 3.77(s, 3H).<br>ESI-MS m/z calcd for $C_{18}H_{18}ClNO_5$ 363.09, found 328.3[M + H]$^+$ |
| 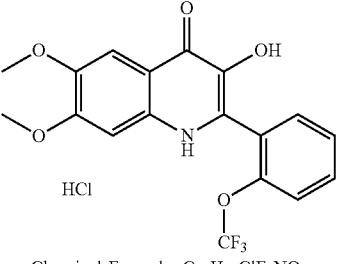<br>Chemical Formula: $C_{18}H_{15}ClF_3NO_5$<br>Exact Mass: 417.0591<br>Molecular Weight: 417.7652<br>Compound 52 | $^1$H-NMR (300 MHz, DMSO): δ 7.74-7.70(m, 2H), 7.63-7.54(m, 3H), 7.16-7.13(m, 1H), 3.91-3.88(m, 6H).<br>ESI-MS m/z calcd for $C_{18}H_{15}ClF_3NO_5$ 417.06, found 382.3[M + H]$^+$ |

Biological Examples of the Invention

Another aspect of the invention relates to methods of inhibiting NADPH oxidase (NOX) in cell, comprising the step of administering to the cell an effective amount of the compound or the pharmaceutical composition according to embodiments of the present application.

Within the context according to the present application, samples with NOX activity include enzymes; tissue or cell cultures; biological samples such as biological material samples (blood, serum, urine, cerebrospinal fluid, tears, sputum, saliva, tissue samples, and the like); laboratory samples; biological samples such as extracts of cells, particularly recombinant cells expressing NOX; and the like. Samples can be contained in any medium including water and organic solvent\water mixtures.

If desired, the NOX inhibiting activity of a compound of the present disclosure after use of the compound or the composition can be observed by any method including direct and indirect methods of detecting such activity. Quantitative, qualitative, and semiquantitative methods of determining such activity are all contemplated. Typically one of the methods described below are applied, however, any other method such as observation of the physiological properties of a living organism are also applicable.

The NOX inhibiting activity of a compound or a composition according to the present application can be measured using standard screening protocols that are known. For example, the NOX inhibiting activity of a compound or a composition can be measured using the following general protocols.

NOX1 HT29 Cell-Based Assay:

HT29 cells were cultured in T75 flask (Corning) and when 70-80% confluence was reached, cells were trypsinized, harvested in HBSS and counted. $1-2 \times 10^5$ cells were dispensed into individual wells in 70 μl final volume (96-well plates, white Corning). Cells were treated for 30-60 mins at 37° C. with 10 μl of GKT137831, DMSO and test compounds from their respective assay plates. This will correspond to a final concentration of 100 nM, 1000 nM GKT137831 or test compounds, and 0.1% DMSO. 20 μL of a mixture containing 100 μM luminol plus 0.4 units of HRP (final concentration) was added. Luminescence was quantified using a SpectraMax i3 Multiplate reader (Molecular Devices, Sunnyvale, Calif., USA). As designed, compounds that inhibit NOX1 activity will reduce cellular ROS production, leading to reduced probe-ROS interactions and reduced well luminescence. Compounds were tested in duplicate at a concentration of 100 nM and 1000 nM. DMSO and GKT137831 wells were applied as negative and positive controls, and the activities measured were set to 0% and 100%, respectively.

NOX2 HL60 Cell-Based Assay:

HL-60 cells, rich in NOX2 expression, was stimulated to undergo oxidative burst by phorbol myristate acetate (PMA). The ROS produced during this process was measured using the $O_2^-$-specific chemiluminescent probe L012. L012 was added to DMSO-differentiated HL-60 cell suspensions to a final concentration of 100 μM. Then, 80 μL aliquots of cell suspension ($2.5 \times 10^5$ cells) were transferred to individual wells of a 96-well plate. Test compounds were directly added to the wells at the specified concentrations. Following a 30-60 mins incubation at 37° C. in the dark, the oxidative burst was initiated by the addition of 10 ng/mL PMA, and the chemiluminescence signal was recorded every 5 min over a period of 60 mins in a SpectraMax i3 Multiplate reader (Molecular Devices, Sunnyvale, Calif., USA).

NOX4 HEK293 Overexpression Cell-Based Assay:

Extracellular $H_2O_2$ measurement using Amplex™ Red Hydrogen Peroxide/Peroxidase Assay Kit (Catalog number: A22188; Invitrogen, Carlsbad, Calif., USA) was used to detect extracellular $H_2O_2$ release by HEK293 cells stably overexpressing NOX4. NOX4 clonal cells in log-phase growth were trypsinized, washed, and dispersed thoroughly. Following trypsinization, the cells ($3\times10^4$) were resuspended in 100 μL of 1× Krebs-Ringer phosphate glucose (KRPG) buffer containing various concentrations of GKT137831 or test compounds and incubated at 37° C. for 30 min. Cells were mixed with 100 μL of Amplex Red reagent solution containing 50 μM Amplex Red and 0.1 units/mL of HRP in KRPG buffer; each assay condition was evaluated induplicate. The samples were incubated at 37° C. for 90 mins in the dark, and then centrifuged at 2,500 g for 5 mins. The supernatants were loaded to a 96 well plate, and then measured using a SpectraMax i3 Multiplate reader (Molecular Devices, Sunnyvale, Calif., USA) at 530 nm excitation and 590 nm emission respectively. DMSO and GKT137831 wells were applied as negative and positive controls, and the activities measured were set to 0 and 100, respectively.

Representative examples of the NOX inhibiting activity of the compounds of Formula I are shown in the Table below. Wherein, A indicates that the percent of inhibition of NOX by the compounds is larger than or equals to 80%; B indicates that the percent of inhibition of NOX by the compounds ranges from 50% o to 79% o; C indicates that the percent of inhibition of NOX by the compounds ranges from 2000 to 49%; and D indicates that the percent of inhibition of NOX by the compounds is smaller than or equals to 19% o.

Inhibition of NOX Activity by the Compounds

| Compound # | % Inhibition NOX1 | | % Inhibition NOX2 | | % Inhibition NOX4 | |
|---|---|---|---|---|---|---|
| (nM) | 100 | 1000 | 100 | 1000 | 100 | 1000 |
| 2 | A | A | D | B | C | A |
| 3 | C | A | C | A | D | B |
| 4 | B | A | D | B | D | A |
| 5 | A | A | D | A | C | A |
| 6 | A | A | D | D | C | B |
| 7 | A | A | D | B | B | A |
| 8 | C | A | D | D | D | B |
| 45 | D | A | D | D | C | B |
| 9 | A | A | D | A | B | A |
| 46 | A | A | D | A | B | B |
| 10 | A | A | D | C | C | A |
| 11 | D | B | D | D | C | A |
| 12 | D | A | D | D | D | A |
| 13 | A | A | D | A | C | A |
| 47 | A | A | D | A | C | A |
| 14 | D | A | D | D | D | D |
| 15 | A | A | C | A | C | A |
| 32 | D | B | C | C | D | C |
| 16 | A | A | C | A | B | B |
| 17 | A | A | C | B | B | B |
| 33 | A | A | D | B | D | B |
| 39 | D | A | D | D | D | B |
| 18 | A | A | C | B | C | B |
| 19 | A | A | D | B | D | B |
| 20 | A | A | B | A | C | B |
| 21 | A | A | D | B | C | A |
| 22 | A | A | C | A | C | A |
| 29 | A | A | C | B | B | B |
| 23 | A | A | B | A | B | B |
| 34 | D | D | D | D | D | D |
| 51 | A | A | C | A | D | B |
| 24 | A | A | C | A | C | B |
| 25 | B | A | D | B | D | C |
| 30 | D | A | B | A | D | D |
| 37 | D | A | B | A | D | B |
| 26 | A | A | B | A | C | A |
| 52 | A | A | C | B | C | B |
| 27 | A | A | D | A | C | A |
| 42 | A | A | B | A | B | B |
| 43 | A | A | B | A | B | B |
| 44 | A | A | C | A | B | B |
| 40 | D | A | C | B | D | B |
| 48 | A | A | C | B | C | A |
| 41 | A | A | C | A | B | B |
| 38 | D | D | D | D | D | C |
| 35 | D | D | D | D | D | D |
| 49 | A | A | D | A | C | B |
| 50 | A | A | B | A | B | B |
| 36 | C | A | C | A | D | B |

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A compound of Formula II, or a geometric isomer, enantiomer, diastereomer, racemate, atropisomer, pharmaceutically acceptable salt or solvate thereof:

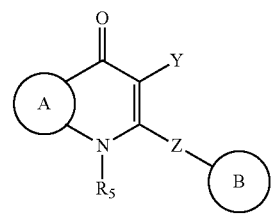

II

Wherein

A is a methylenedioxybenzene moiety, an ortho-dimethoxybenzene moiety, or a trimethoxybenzene moiety;

B is a phenyl group substituted with one or more nitro, methyl, $CF_3$, halogen, pyrrolidine, $OR_{31}$ $NR_{21}R_{22}$ or $SO_2R_{21}$;

$R_{21}$ is H, methyl, ethyl, n-propyl, or $CF_3$;

$R_{22}$ is H;

$R_{31}$ is methyl, ethyl, n-propyl, or $CF_3$;

Y is OH or $NH_2$;

Z is nil; and $R_5$ is H or $C_1$-$C_{10}$ alkyl.

2. The compound of claim 1, wherein $R_5$ is H or methyl.

3. The compound of claim 1, wherein the compound is selected from a group consisting of:
2
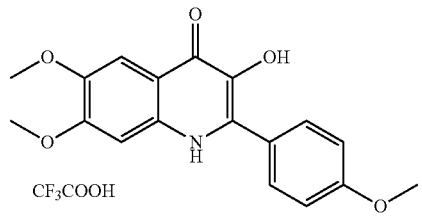
CF₃COOH
4
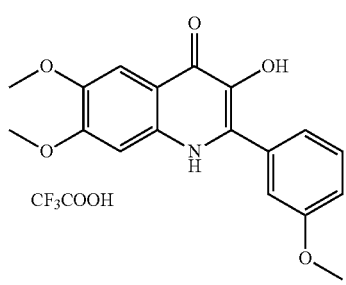
CF₃COOH
5
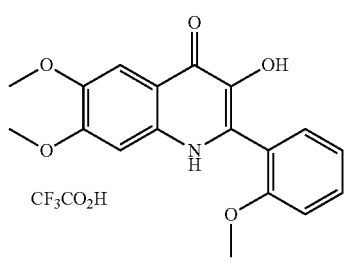
CF₃CO₂H
6
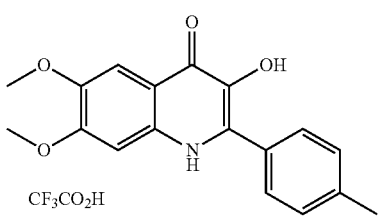
CF₃CO₂H
8
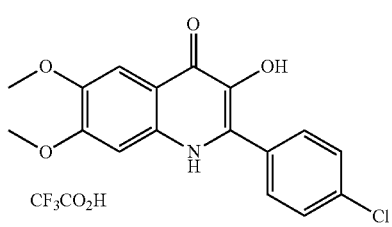
CF₃CO₂H
45
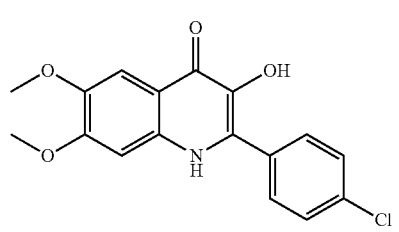
-continued
9
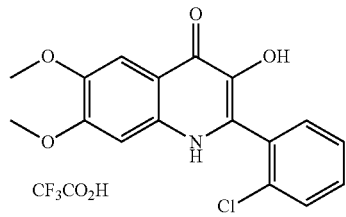
CF₃CO₂H
46
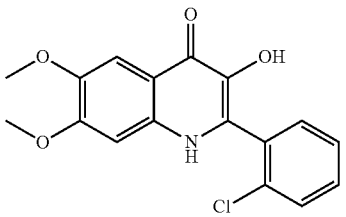
11
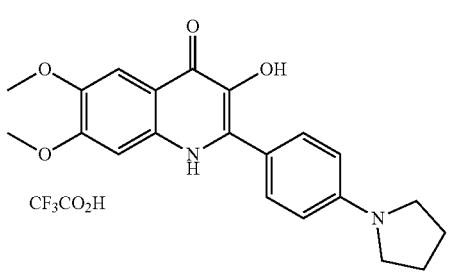
CF₃CO₂H
12
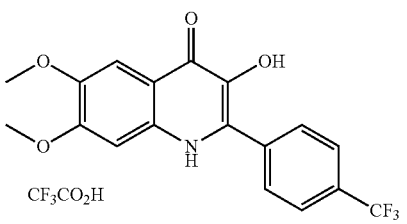
CF₃CO₂H
13
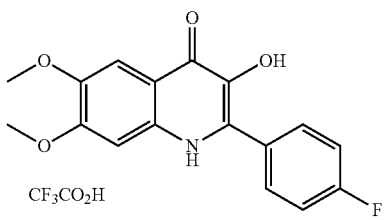
CF₃CO₂H
47
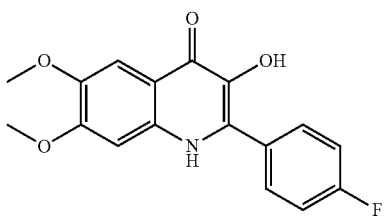

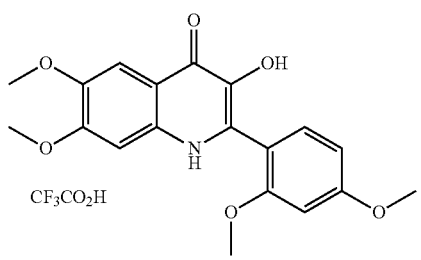
15
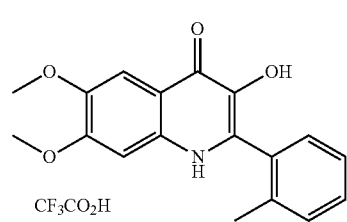
16
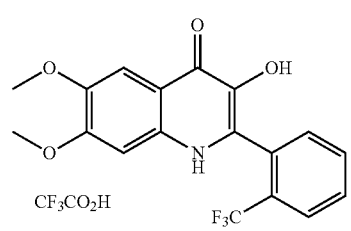
17
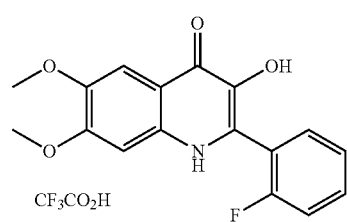
18
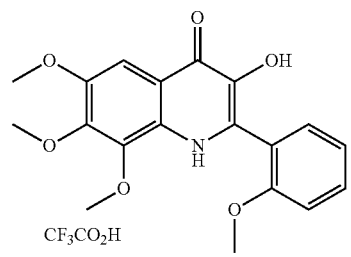
19
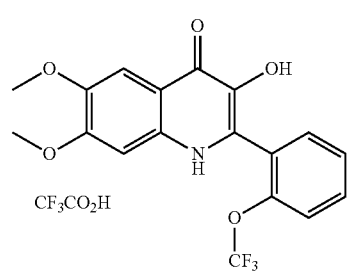 [SMILES: COc1cc2[nH]c(-c3ccccc3OC(F)(F)F)c(O)c(=O)c2cc1OC ; Cl]
20
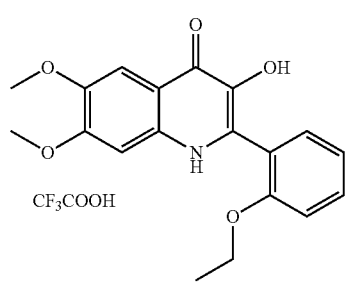
21
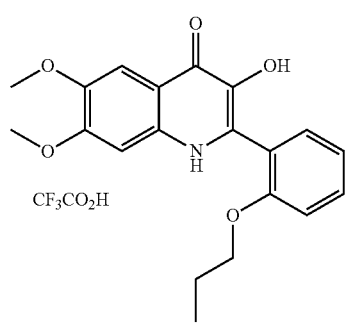
22
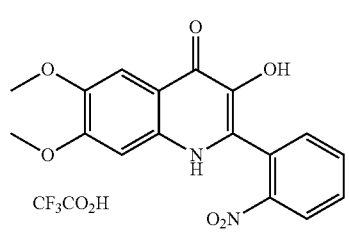
29
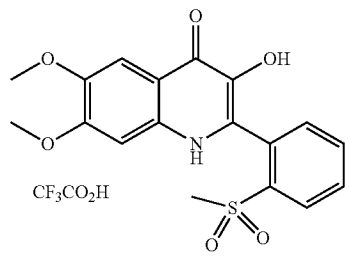
23
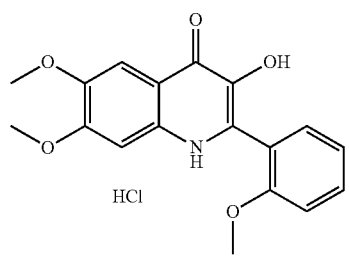
51
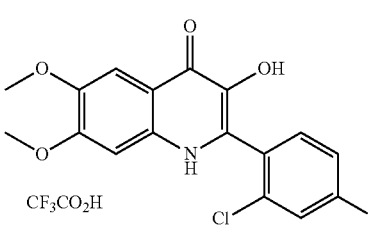
24

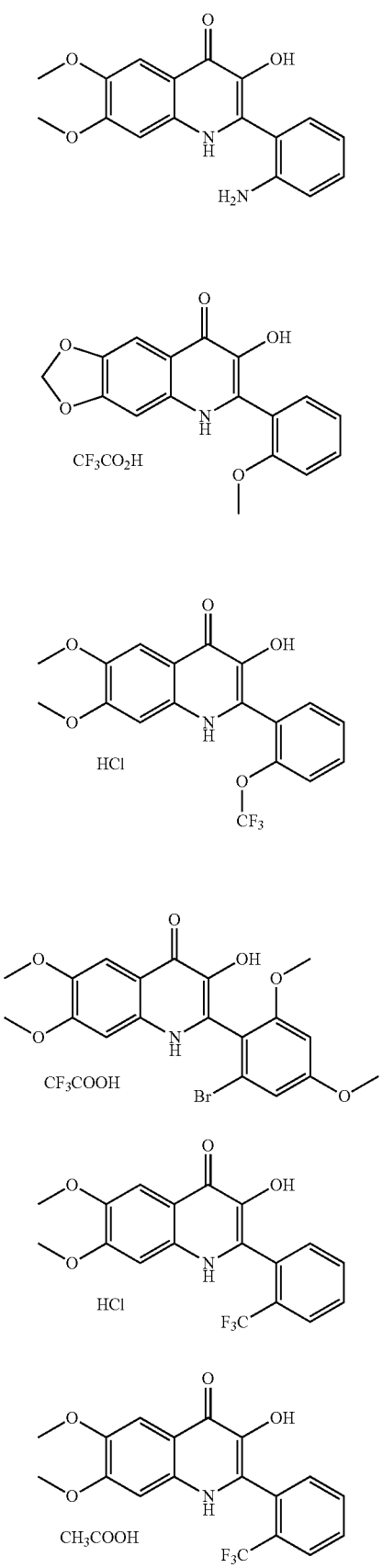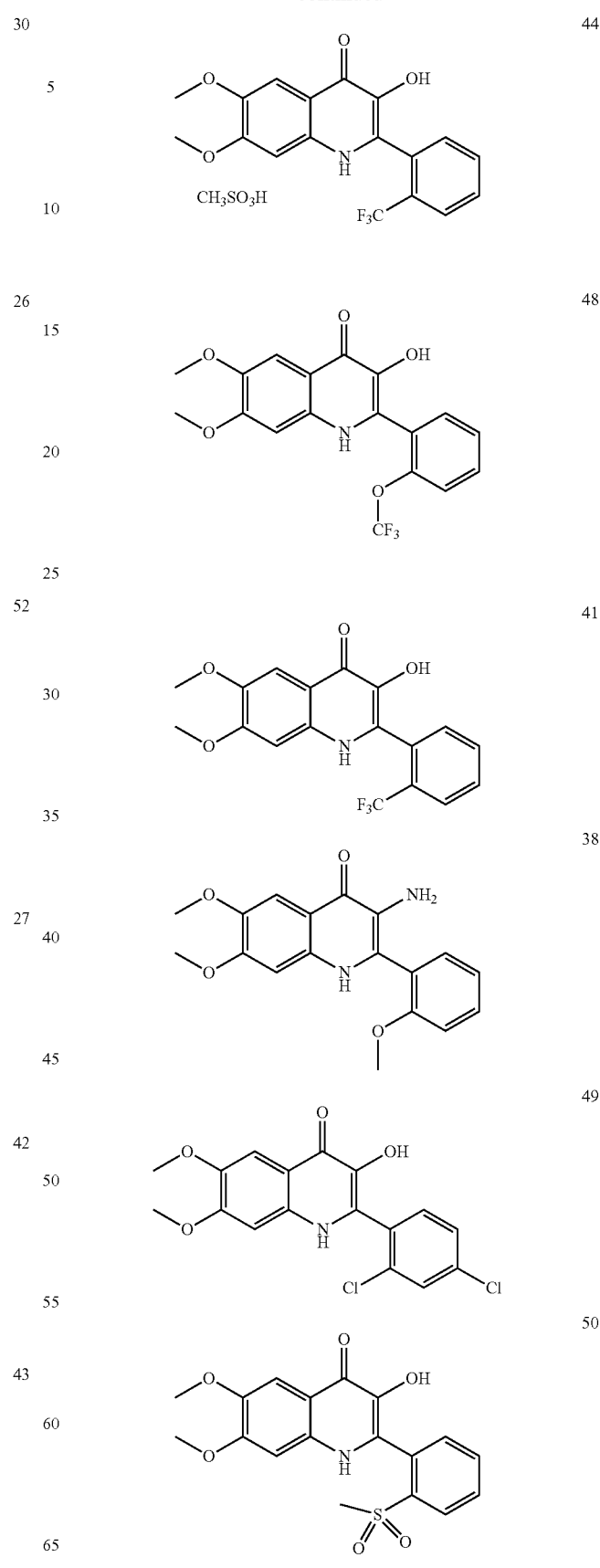

-continued
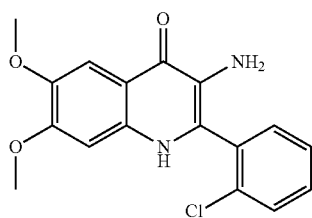
36
4. A pharmaceutical composition comprising a compound of claim 1 and at least a pharmaceutically acceptable excipient or carrier.
5. The compound of claim 3, wherein the compound is selected from a group consisting of:
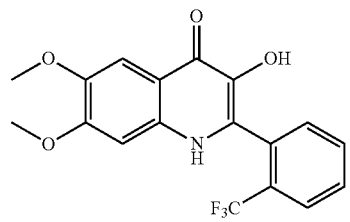
41
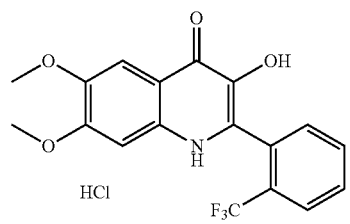
42
-continued
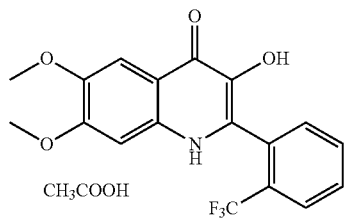
43
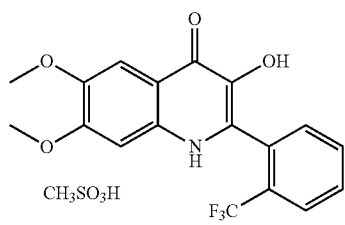
44
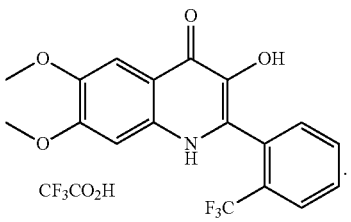
17
* * * * *